(12) United States Patent
Flam et al.

(10) Patent No.: US 8,491,513 B2
(45) Date of Patent: Jul. 23, 2013

(54) APPARATUS AND METHODS FOR PREVENTING AND/OR HEALING PRESSURE ULCERS

(75) Inventors: Eric Flam, East Brunswick, NJ (US); Oliver Bodine, Huntington, NY (US); Henry I. Schanzer, Edison, NJ (US)

(73) Assignee: Eric Flam, East Brunswick, NJ (US)

( * ) Notice: Subject to any disclaimer, the term of this patent is extended or adjusted under 35 U.S.C. 154(b) by 0 days.

(21) Appl. No.: 13/199,722

(22) Filed: Sep. 7, 2011

(65) Prior Publication Data

US 2012/0060849 A1     Mar. 15, 2012

Related U.S. Application Data

(63) Continuation of application No. 11/518,681, filed on Sep. 11, 2006, now Pat. No. 8,070,701, and a continuation of application No. 09/818,722, filed on Mar. 27, 2001, now Pat. No. 7,141,032.

(60) Provisional application No. 60/192,827, filed on Mar. 29, 2000.

(51) Int. Cl.
*A61F 5/00* (2006.01)

(52) U.S. Cl.
USPC ............................................. 602/23; 602/27

(58) Field of Classification Search
USPC ................ 128/845, 846, 882; 602/19, 23–27, 602/60–61
See application file for complete search history.

(56) References Cited

U.S. PATENT DOCUMENTS

| | | | | |
|---|---|---|---|---|
| 3,148,678 A | * | 9/1964 | Roberts | 602/29 |
| 3,998,219 A | * | 12/1976 | Mercer et al. | 602/6 |
| 4,076,022 A | * | 2/1978 | Walker | 128/892 |
| 4,730,610 A | * | 3/1988 | Graebe | 128/882 |
| 4,912,788 A | * | 4/1990 | Lonardo | 5/653 |
| 5,156,629 A | * | 10/1992 | Shane et al. | 623/37 |
| 5,289,828 A | * | 3/1994 | Toth | 5/624 |
| 5,725,486 A | * | 3/1998 | Engelman | 602/5 |
| 5,882,324 A | * | 3/1999 | Baranowski | 602/65 |
| 6,197,064 B1 | * | 3/2001 | Haines et al. | 623/20.31 |
| 6,346,210 B1 | * | 2/2002 | Swartz et al. | 264/486 |
| 6,531,643 B2 | * | 3/2003 | Suzuki | 604/381 |

* cited by examiner

*Primary Examiner* — Michael A. Brown
(74) *Attorney, Agent, or Firm* — Henry I. Schanzer

(57) ABSTRACT

Protective devices, to protect a body part having a bony portion with a soft tissue layer between the bony portion and an outer skin layer, have an inner surface which conforms to the body part to be protected and are applied to the body part to reduce pressure exhibited at the interface between the bony portion and the soft tissue layer, across the soft tissue and outer skin layers and at the interface between the outer skin layer and a support surface. The protective devices may be made of any material suitable for distributing the weight of the body part over an extended area and volume so as to decrease the pressure about the bony portion.

20 Claims, 41 Drawing Sheets

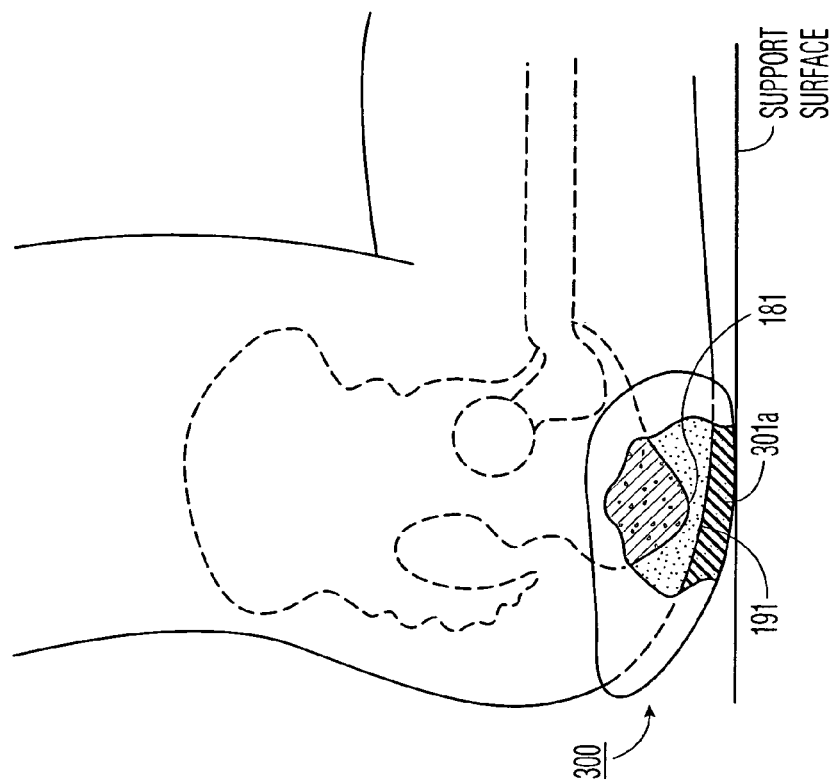
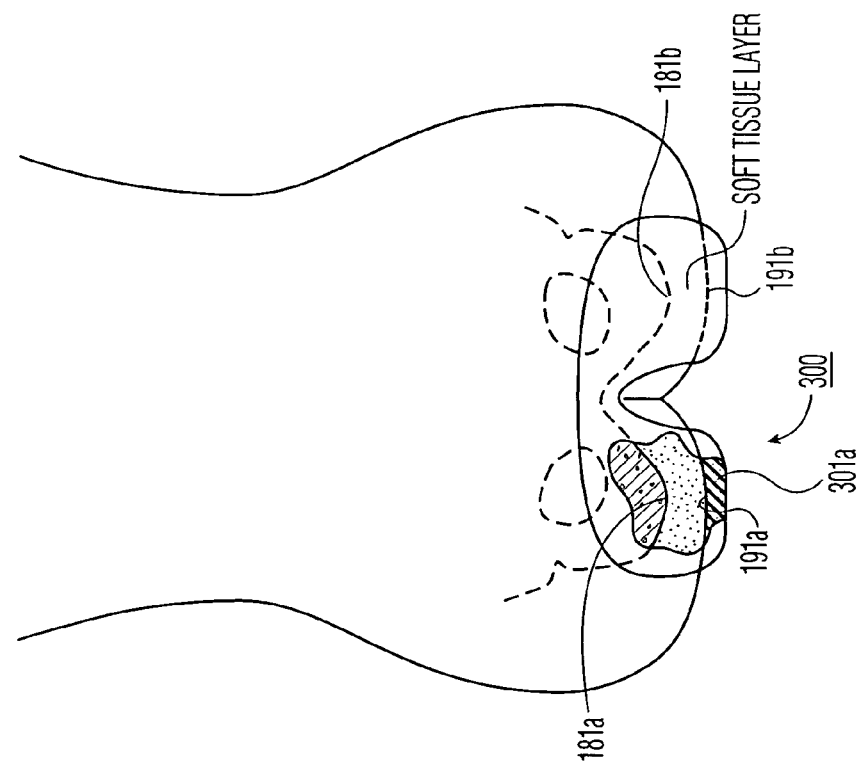
FIG. 8A
FIG. 8B

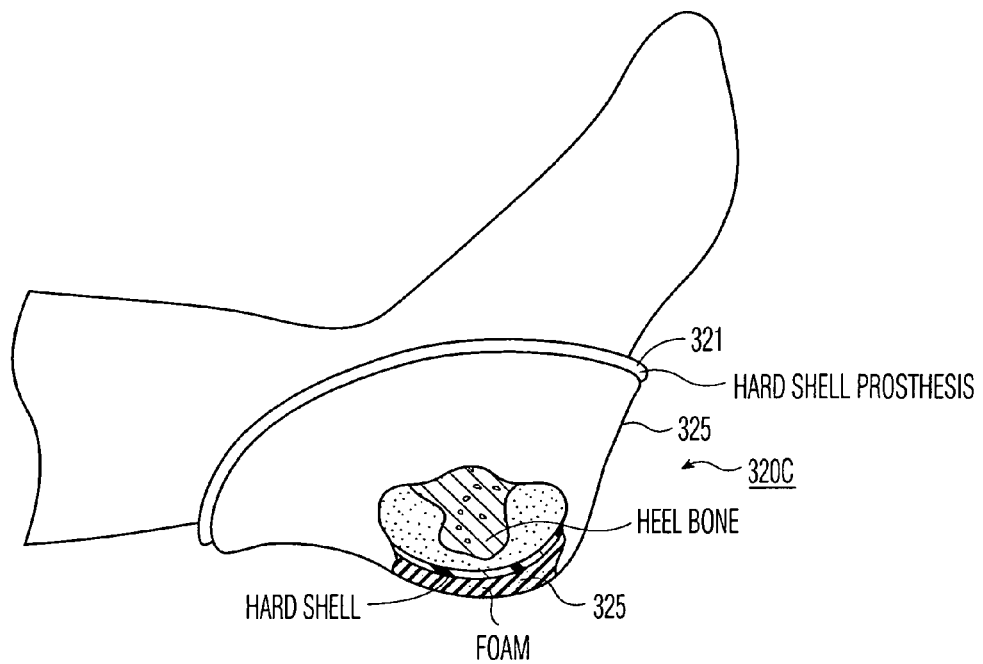
FIG. 14G
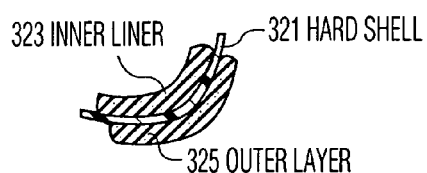
FIG. 14G1

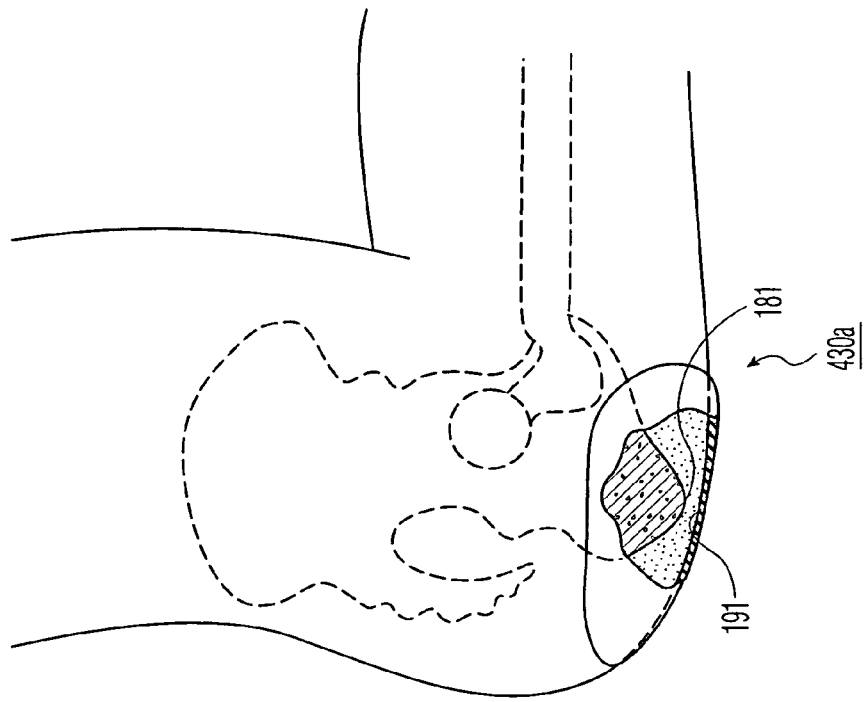
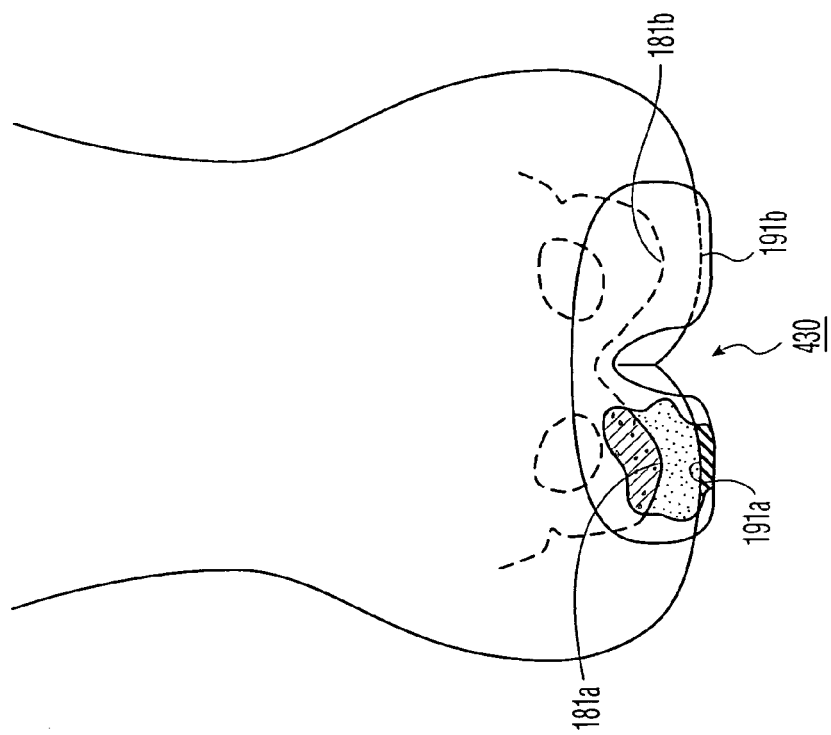

FIG. 24D1

APPARATUS AND METHODS FOR PREVENTING AND/OR HEALING PRESSURE ULCERS

This application is a continuation of application Ser. No. 09/818,722 filed Mar. 27, 2001 now U.S. Pat. No. 7,141,032 (which claimed the benefit of U.S. Provisional Application No. 60/192,827 filed Mar. 29, 2000) which is now U.S. Pat. No. 7,141,032 and of application Ser. No. 11/518,681 filed Sep. 11, 2006 now U.S. Pat. No. 8,070,701.

BACKGROUND OF THE INVENTION

This invention relates to devices intended to be applied to selected parts of a human body for preventing and/or healing pressure ulcers and to methods for determining the size and shape of the devices to be used.

Pressure ulcers also referred to as "bed sores" or decubitus ulcers may be developed by individuals confined for an extended period of time to a particular position in a bed or chair. When a person is bed ridden or wheel chair bound due to such causes as an accident, illness, or extensive period of recovery from surgery, the body tends to be immobilized for an extended period of time. It has been noted that pressure ulcers occur most frequently in certain parts of the body, such as the heel and ankle, the trochanter, the sacrum, the scapulae, at the elbows, knees, occiput, ischial tuberosites and at the coccyx. As presently understood, the weight overlying these body parts exerts sufficient pressure on the underlying soft tissue layers to cause an interruption of the flow of blood to and through the soft tissue layers causing the development of a condition generally referred to as pressure ulcers.

A significant amount of work has been done to improve support structures (e.g., beds and wheelchairs) in order to decrease the likelihood of persons lying on these support structures from developing pressure ulcers. However, it is evident that individuals vary greatly in height, weight and shape. As a result, a support structure, such as a bed, suitable for one person may not be suitable for another person. Furthermore, even if a bed is custom made for an individual, as the individual moves about the bed (up, down, sideways, or at an angle) the need to relieve pressure at and along certain points of the individual's body may no longer be met.

SUMMARY OF THE INVENTION

Applicants' invention resides, in part, in the recognition that certain parts of the body are prone to the development of pressure ulcers (i.e., bedsores) and that these parts of the body may be effectively protected by attaching or inserting a suitable protective device (e.g., padding and/or cushion and/or cast) between the body part and an underlying support structure (e.g., a bed or chair) in order to reduce the pressure exerted at the bone-soft tissue interface, across the corresponding soft tissue layer, and at the interface between the outer skin and the protective device.

Applicants' invention also resides, in part, in the recognition that: (a) the body part prone to develop pressure ulcers often includes a bony prominence and, generally, there is often only a thin layer of soft tissue between the bony prominence and the corresponding outer skin layer; (b) when such a body part rests on a support structure (e.g., bed or chair), the weight of the body part including the weight of bony material exerts pressure on the soft tissue layer underlying the bony prominence; (c) the pressure developed across the bony-prominence-soft-tissue interface and across the soft tissue is a function of the thickness of the soft tissue layer and the overlying weight; and (d) the pressure developed at various layers below the bony material is a function of how the weight gets distributed along and across the soft tissue layer resting on a support surface.

Applicants' invention also resides, in part, in the recognition that, as to a particular body part, the weight from the overlying flesh and bony prominence exerted downward and outward from the bony prominence through the underlying soft tissue layer results in pressure(s) which may be reduced by the application of a protective device ("prosthesis") to the particular body part. The prosthesis functions to increase the area over which the weight of the body part is distributed thereby decreasing the pressure at the interface between the bony prominence and the underlying soft tissue layer, across the soft tissue layer and at the contact area between the skin and any underlying support surface. In effect, the prosthesis functions to add thickness to the soft tissue over which the weight of the body part is distributed thereby decreasing the pressure at the interface between the bony prominence and the underlying soft tissue layer across the soft tissue layer and at the contact area between the skin and any underlying surface.

Prostheses embodying the invention may be made of soft foam like materials ("mushy" foams) which provide good weight distribution; but, the softer the foam the thicker it has to be to provide the desired degree of protection. For best results, the inner surface of these "soft" protective devices should conform to the shape of the body part to be protected. However, this is not a necessary condition due to the "conforming" nature of the mushy foams.

Alternatively, prostheses embodying the invention may be formed with a hard, relatively thin, shell which provides good weight distribution if the prosthesis is contoured to conform to the body part which it is intended to protect.

Materials ranging in stiffness between the "soft" foam and the "hard" shell having appropriate thicknesses may be used to form prostheses providing the desired pressure reduction in accordance with the invention.

The invention is also directed to the identification of certain points/parts of the body most susceptible of developing pressure ulcers, and to the application, or attaching, of an appropriate prosthesis to one or more of these parts of the body to reduce the pressure in a controlled manner. Protective devices (prostheses) embodying the invention may be applied like a bandage to the body part and may be secured to the body part in any one of numerous ways. Applicant's invention also resides in methods for evaluating certain patients to ascertain which parts of their body are prone to developing pressure ulcers and to determining the size and shape of appropriate protective devices for these patients.

The application of a prosthesis embodying the invention to various body parts of a person enables that person to be placed on virtually any practical (or available) support structure (e.g., a hospital bed) for an extended period of time with little (or no) likelihood of the person developing a pressure ulcer.

BRIEF DESCRIPTION OF THE DRAWINGS

In the accompanying drawing like reference characters denote like components.

FIG. 8A is a cross sectional cutaway view of the ischial region with a prosthesis in place;

FIG. 8B is a cross sectional diagram of an ischium with a prosthesis in place;

FIG. 14G is a cutaway view of the heel with a hard shell prosthesis and a foam cover over the prosthesis;

FIGS. 16A, 16B, 16C, 16D are various views of the ischial region and a "hard" shell prosthesis for protecting that region;

DETAILED DESCRIPTION OF THE INVENTION

Ankle/Heel Prostheses

Figure 1A:
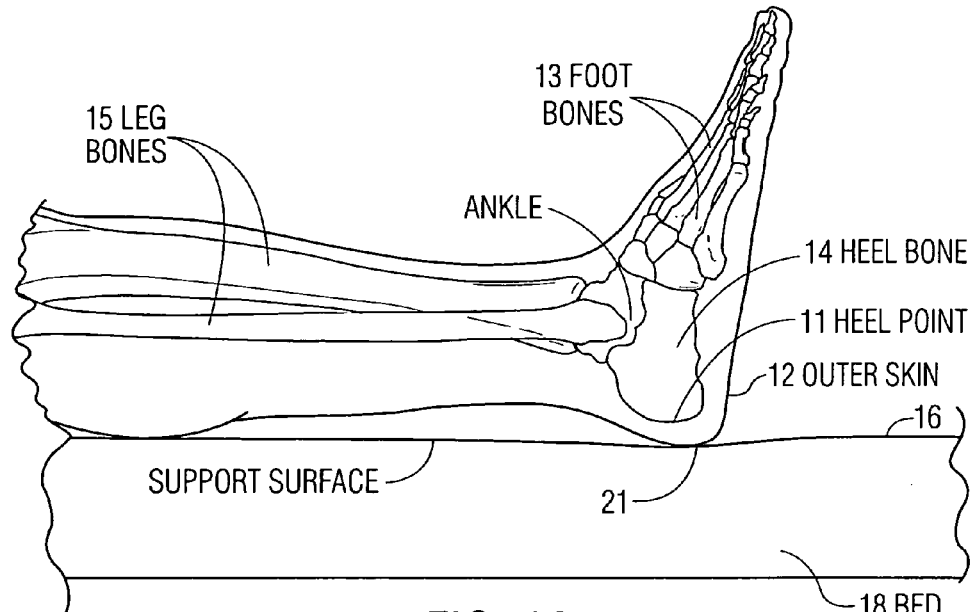
FIG. 1A is a simplified cross-sectional drawing of an ankle/heel region of a foot and a portion of a leg illustrating a problem that is resolved by the invention.

Applicants' invention will be explained by first referring to FIGS. 1A, 1B, 1C, 1D and 1E which illustrate that the weight (W) developed in the ankle and heel region (including the lower leg and foot) when the heel rests on a relatively firm support surface 16 is distributed over a relatively narrow cone like section extending outward from the bone region towards the support surface 16. For purpose of illustration, it is assumed that the weight due to the skin and soft tissue overlying foot bones 13 and leg bones 15 and the weight due to components from bones 13 and 15 is transferred to the heel bone 14. The heel bone is shown as a hemisphere-like structure, terminating in a heel point/region 11 in FIG. 1A. When the back of the heel rests on a relatively firm support surface, 16, of a bed 18, the weight onto and from point 11 is distributed along a relatively narrow cone-like portion of the soft tissue underlying point 11 (hatched region in FIGS. 1B, 1C, 1D). Heel point 11 is not a sharp point but a rather small region and the weight at point 11 would extend over a small arc illustrated as going from 101 to 103 and be applied through the portion of the soft tissue layer (shown as a hatched region) to outer skin layer 12. Soft tissue or soft tissue layers, as used herein and in the claims, refers to a composite material comprising multiple layers of skin, fat and muscle tissue located between the skeletal system [bone(s)] and the outer surface of the body (skin, or outer skin). The outer skin layer of the heel region makes contact with the underlying support surface 16 at a contact surface 21 defining a relatively small circular or elliptical area. For ease of illustration, it is assumed that the weight is distributed across the soft tissue layers extending from point 11 to contact surface 21. As shown in FIGS. 1B, 1C, 1D and 1E, at contact surface 21, the overlying body weight would be distributed over a region extending from 201 to 203.

Applicants recognized that the pressure exerted at any point below the heel point is a function of the weight (W) divided by the area (A) over which the weight is distributed. Applicants further recognized that, in many instances, the pressure is greatest at the interface between the bony point 11 and the soft tissue layer immediately below the bony point because much of the weight is concentrated at the bony prominence and the area over which the weight (W) is distributed is least at that point. In effect, this makes the interface between the bone and the soft tissue (i.e., the area at, or just below, heel point 11, in FIGS. 1A, 1B, 1C, 1D) the most susceptible to ulceration, at least for this example.

Figure 2A:
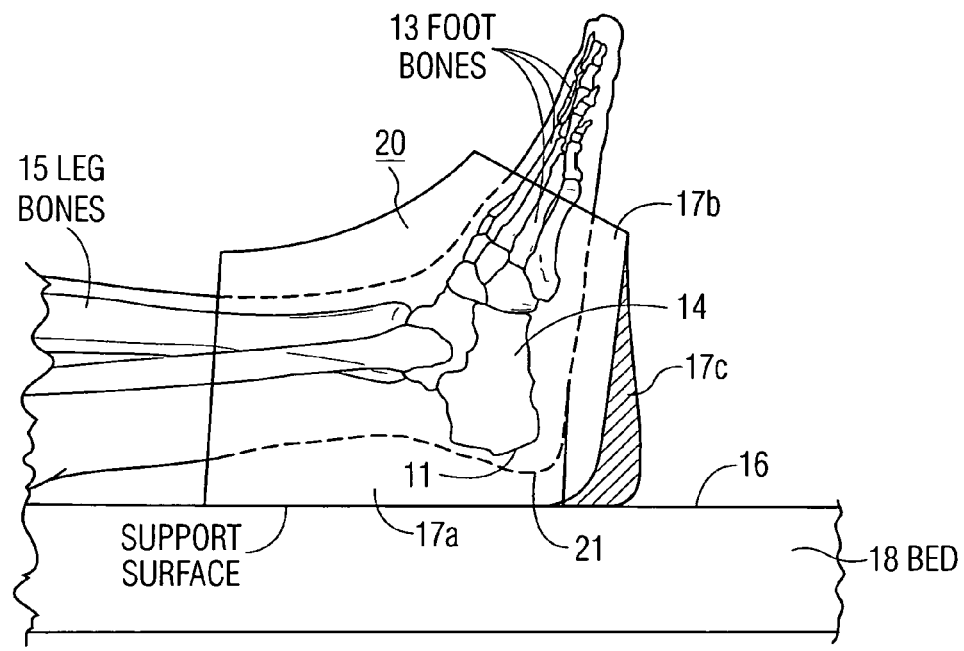
FIG. 2A is a simplified cross sectional diagram of a prosthesis embodying the invention positioned to protect the heel and ankle region.

Applicants' invention is now illustrated with reference to FIG. 2A which is a simplified cross sectional view of a prosthesis 20 made of a compliant soft, mushy, foam material, applied to an ankle/heel region. As may be observed from FIG. 2A, the significant portion of prosthesis 20 is the portion 17 which extends below the back of the lower leg, ankle, heel and arch of the foot. The portion 17 includes a first section, 17a, which underlies the heel, the ankle and the back of the lower leg, a second section, 17b, which underlies the arch and back of the foot, and a third section, 17c, which provides wedging type support between sections 17a and 17b and support surface 16. The prosthesis functions, in effect, as an extension of the soft tissue layer lying under bones 13 and 15 and heel point 11. As illustrated in FIG. 2A, the prosthesis adds substantial volume to the underside of the heel distributing the weight and cushioning the underside of the heel.

The inner surfaces of sections 17a and 17b of the prosthesis 20 are shaped to conform to, or to be conformable with, the outer shape of the foot with which they are in contact. Ensuring conformance and good contact between the inner surfaces of the prosthesis and the outer skin layer results in better weight distribution and a larger decrease in the pressure at the bony prominence-soft tissue interface (11) and across the soft tissue layer between regions 11 and 21.

The outer surface of prosthesis section 17a, in contact with the support surface 16, conforms to (or is conformable with) surface 16. Section 17b in conjunction with section 17c is designed to provide additional support for the weight of the foot. Sections 17a, 17b, and 17c ensure that the weight present at the greatest point of concentration (e.g., heel point 11) is distributed over the largest possible area. As discussed below, if the first portion 17a of the prosthesis is sufficient to provide the necessary protection (i.e., pressure relief), then sections 17b and 17c may not be needed.

Figure 1B:
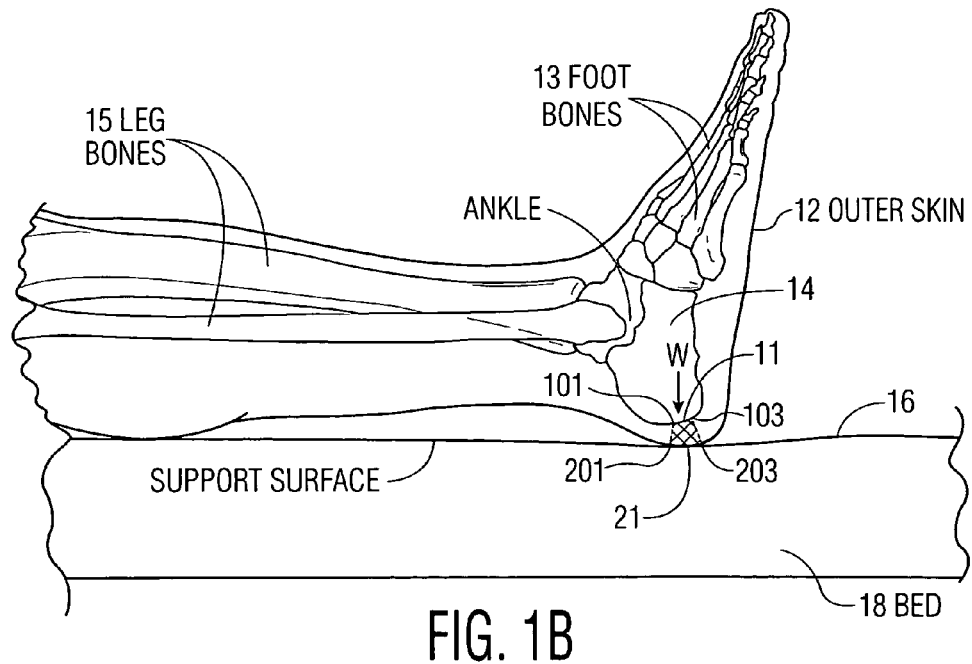
FIGS. 1B, 1C and 1D are simplified cross sectional diagrams and views showing the weight of the body part exerted on the soft tissue layer below the heel and a representative "pressure cone" in the soft tissue layer associated with the heel point.
Figure 1C:
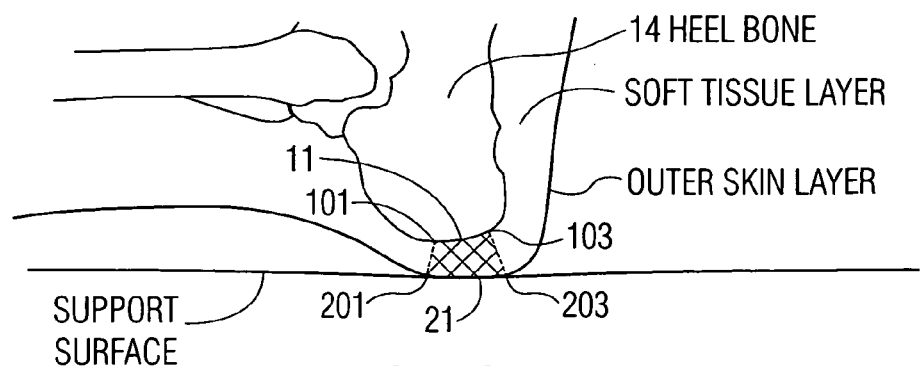
Figure 1D:
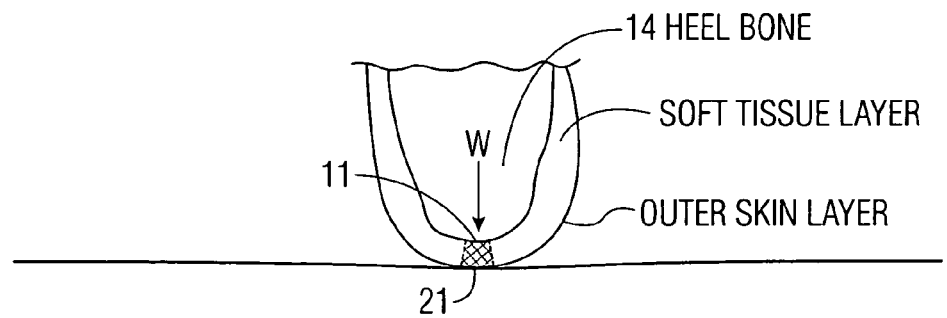
Figure 1E:
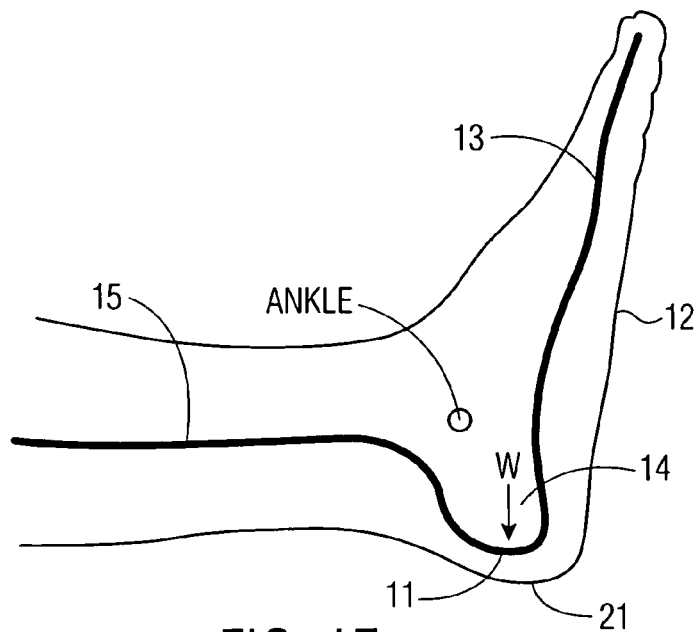
FIG. 1E is a still further simplified diagram of the heel and foot shown in the Figures.
Figure 2B:
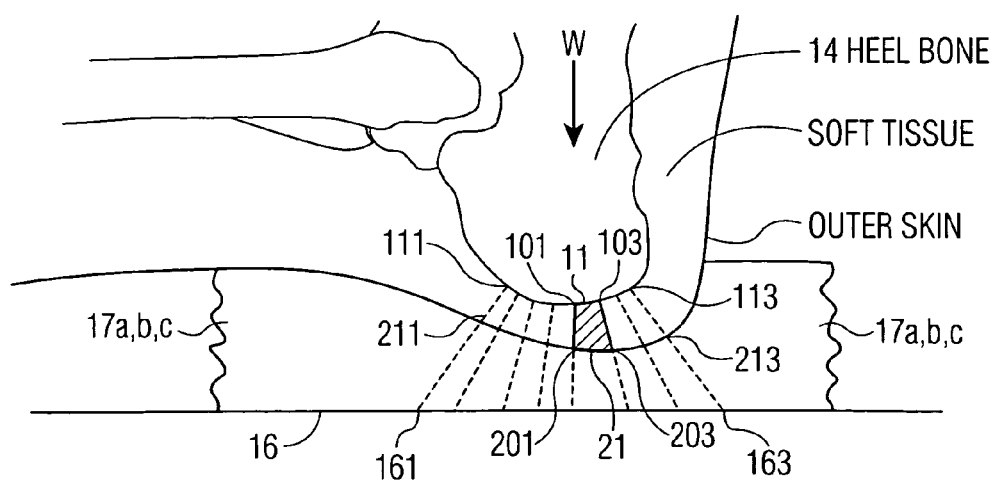
FIG. 2B is an idealized representation of the increase in the weight bearing volume and weight distribution under the heel point resulting from the application of the prosthesis of FIG. 2A.
Figure 3A:
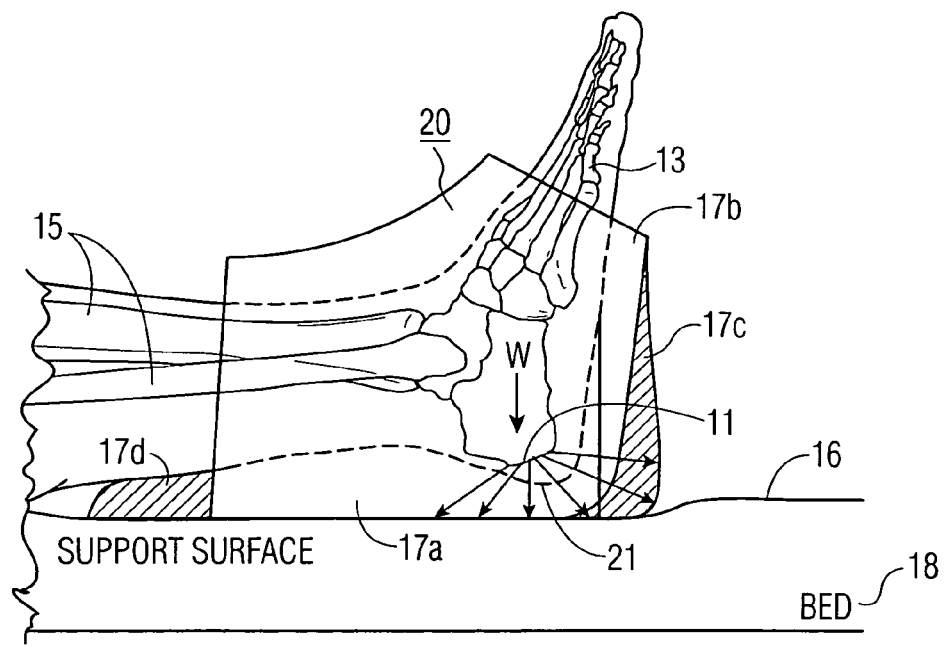
FIG. 3A is a simplified diagram of the prosthesis of FIG. 2A illustrating the distribution of the weight across a larger area in accordance with the invention.

The role of the prosthesis in reducing the pressure at the interface between the heel point 11 and the underlying soft tissue, and across the soft tissue layer between point 11 and the entire outer surface surrounding point 21 may be further illustrated by reference to FIGS. 2A, 2B, 3A, 3B and 3C. In FIG. 3A, lines representing the weight exerted at region 11 are drawn radiating out of point/region 11 with arrow heads pointing away from point 11 and towards surface 16. These lines radiate out across the soft tissue layer below point 11 and across the prosthesis sections 17a, 17b and 17c terminating along the support surface 16. The radiating lines are intended to illustrate how the weight present at point 11 is distributed over an ever increasing area and volume through the soft tissue layer and the prosthesis 17. In a like manner, FIG. 2B illustrates that, with the prosthesis present, the region 11 along which the body part weight is distributed extends from a point 111 to a point 113 along the interface between bony prominence 11 and the underlying soft tissue layer. The length of this arc-like distance is much greater than the length of the arc ranging from 101 to 103 (see FIG. 1B and cross hatched portion of FIG. 2B) when a prosthesis is not present. Furthermore, with a prosthesis in place the arc subtended by the outer skin layer in contact with the prosthesis extends even more. This is shown by the arc extending from point 211 to point 213 which is significantly greater than the distance between 201 and 203 (when there is no prosthesis) shown hatched in FIGS. 1B, 1C and 2B. Also, the prosthesis 17 provides for the distribution of the overlying weight by distributing the weight over an expanding pressure cone having a "diameter" at the contact surface 16 lying between points 161 and 163. This is in sharp contrast to the corresponding length defined by points 201 and 203 in FIGS. 1B and 1C, when the heel lies directly on a support surface. To further illustrate the benefit of weight distribution in accordance with the invention, the "pressure cone" shown in FIGS. 1B and 1C is reproduced and shown hatched in FIG. 2B.

Figure 3B:
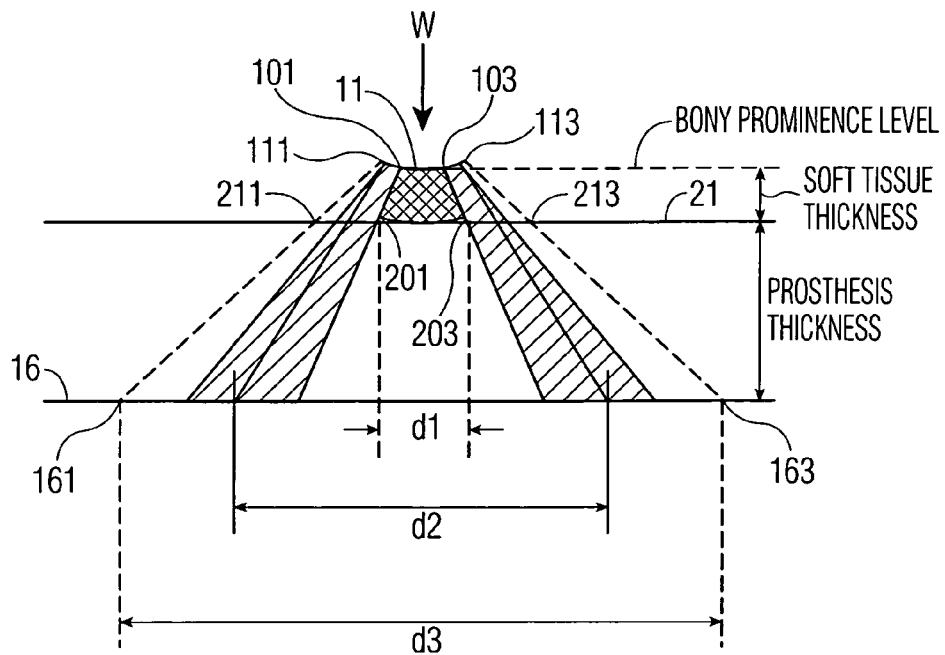
FIGS. 3B and 3C are idealized weight distribution diagrams for different dimensions and/or types of protective devices.

To further illustrate the weight distribution and pressure dilution of the invention, assume (as shown in FIGS. 2B, 3A and 3B) that the weight of the soft tissue and flesh overlying bones 13 and 15 and the weight of bones 13 and 15 is equal to W and is concentrated at a heel point 11. The pressure at point 11 is substantially equal to the weight (W) divided by the area over which the weight W is distributed. As is illustrated by the radiating lines in FIG. 3A, the area of the soft tissue supporting the weight, W, is least at point 11. In going downward from point 11 through the soft tissue layer and then through the prosthesis to support surface 16, the area and volume over which the weight is distributed increases continuously. Assuming that the heel contact point 11 may be represented by a circle, the pressure at any point between the bony point 11 and the surface 16 decreases as a function of the radius. If the function of the radius is the square of the radius, which is the usual case with elastic isotropic materials, then increasing the diameter by a factor of two decreases the pressure by a factor of four. It should be noted that this is for purpose of example only, since the contact may be elliptical or have other shapes.

Figure 3C:
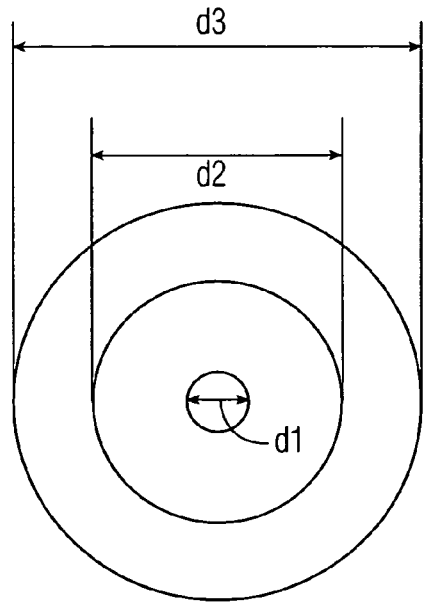

FIGS. 3B and 3C are intended to illustrate that, conceptually, when the foot is lying directly on a support surface 16, without a prosthesis, it results in a narrow pressure cone (shown cross-hatched) supporting the weight W at point 11. At the bony prominence level, the cone extends between 101 and 103 and at the outer skin level 21, the cone diameter extends between points 201 and 203. The final diameter of this narrow "pressure cone" along a plane 21 corresponding to the outer skin layer would be dl, having a surface area corresponding to the showing of the circle with diameter dl in FIG. 3C.

These Figures further illustrate that, conceptually, when a prosthesis is present between the foot and a support surface 16, the area and volume of the pressure cone subtending the overlying weight is a function of the thickness of the prosthesis (this is so, for example, in the case of a prosthesis made of soft, mushy material). When the prosthesis is not optimized for optimum weight distribution (e.g., a prosthesis without section 17b or section 17c), the resulting support "pressure cone" would have a final diameter d2 at plane 16 with a corresponding final surface area as shown in FIG. 3C. When the foot is outfitted with a prosthesis designed to provide optimum weight distribution (e.g., a prosthesis including sections 17a and 17b and of right shape and thickness), a broader "pressure cone" results having, for example, a diameter d3 at the support surface area 16. Since the pressure at any point may be expressed as P=W/A, increasing the radius at any level by a factor of 2, would reduce the pressure at that level by a factor of 4.

An important aspect of the invention is the recognition that using a protective device, such as 20, to distribute the weight present at a certain bony prominence (e.g., 11) over a greater area and volume, can significantly reduce the pressure at the interface between the bony prominence (e.g., 11) and the underlying soft tissue, across the soft tissue, and the interface between the outer skin and the protective device.

It should be appreciated that, in accordance with the invention, pressure problems present at, and due to, other bony prominences of the body may be resolved using appropriate and suitable protective devices/prosthesis for those body parts when in contact with a support surface.

Another aspect of the invention is that the thickness and shape of the protective device 20 may be increased by selected amounts so as to reduce the pressure at the bone-soft tissue interface to less than certain predetermined levels. The comfort of the individual using the prosthesis may be considered in determining the thickness and size/shape of the prosthesis. With respect to FIGS. 2A and 3A, the thickness of the section 17a underneath the foot, to the left of the heel section, raises the end of bone 15 connected to point 11, tending to shift some of the weight away from being concentrated at or about point 11 back and along a portion of the leg which can safely carry a greater amount of weight, because of the thickness of the body part and the increased surface area. However, an important aspect of the protective device embodying the invention is that the weight exerted at a certain point of the body is redistributed at that local point of the body, by increasing the area (and volume) over which the weight is distributed, rather than being shifted from the point in the body where the pressure is "felt" to another point. This ensures that any pressure problem is resolved at its point of origin, rather than being shifted to another location, with uncertain consequences.

As further discussed below, prostheses embodying the invention may be made of many different materials having different softness/hardness features which affect, among others, the thickness of the prosthesis and the extent to which the inner surface of the prosthesis has to conform to the outer shape of the body part to provide best results.

FIG. 3A illustrates that the prosthesis 17 could include, for example, a tapered region 17d to ensure that there are no sharp edges that might prove uncomfortable to the individual outfitted with the prosthesis of the invention. Although not explicitly shown in all the drawings herein, it is understood that prostheses made in accordance with the invention may be shaped to avoid bumps and sharp edges and provide smooth and continuous transitions.

Figure 4:
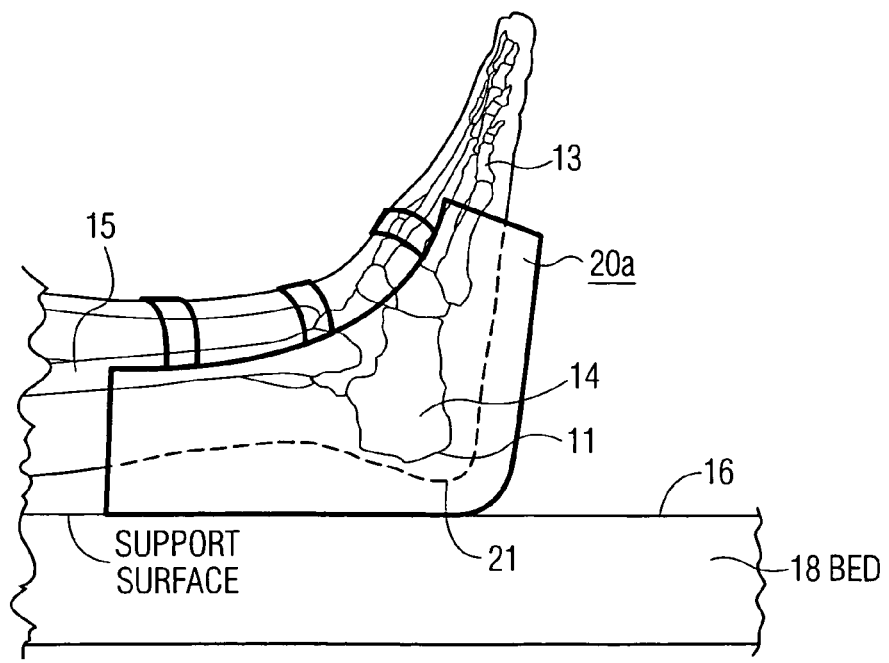
FIG. 4 is a diagram of another prosthesis embodying the invention.

FIG. 4 illustrates that the protective device, 20a, need not cover the top half of the foot, ankle and leg. However, the prosthesis would still protect the heel and the ankle of an individual lying on his/her side. If protecting the ankle is not a concern, the protective device can be cut back so it does not extend so high around the foot.

Figure 5A:
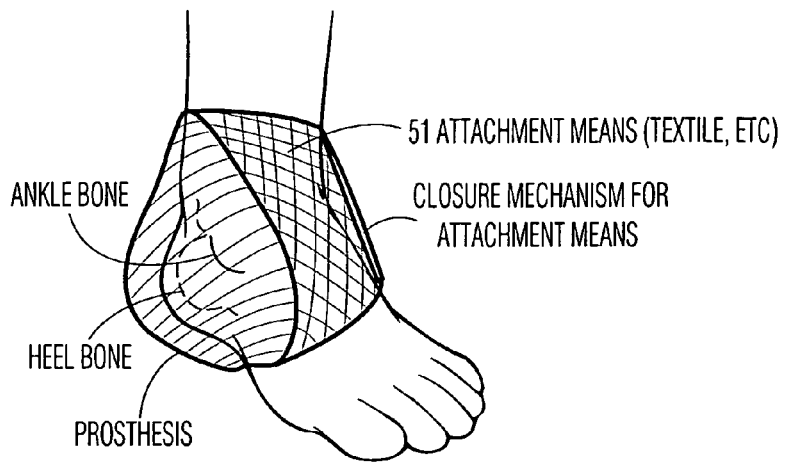
FIGS. 5A, 5B and 5C are diagrams of various protective devices embodying the invention and means for securing them to the foot of an individual.
Figure 5B:
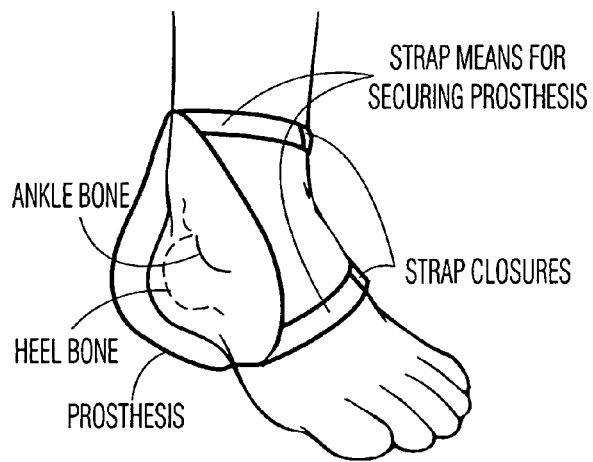
Figure 5C:
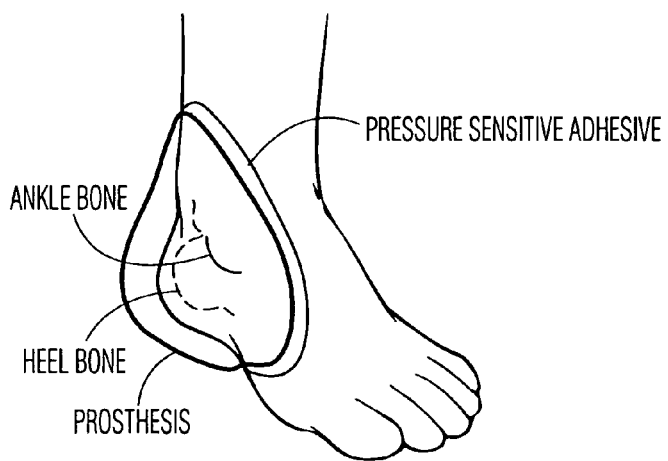

FIGS. 5A, 5B and 5C illustrate various prostheses for protecting the heel and the ankle when the individual either is lying down on his back or on his/her side and attachment means for holding the prostheses in place. In FIG. 5A, a material attached to the prosthesis could include any suitable closure mechanism to hold the prosthesis in place. In FIG. 5B, straps attached to selected points of the prosthesis may be used to hold it conformably and comfortably in place. In FIG. 5C, a boundary region would be included around the periphery of the prosthesis, which perimeter region could include pressure sensitive adhesive in its interior surface for securing the prosthesis to the foot of an individual.

Description of FIGS. 6A-6E

Figure 6A:
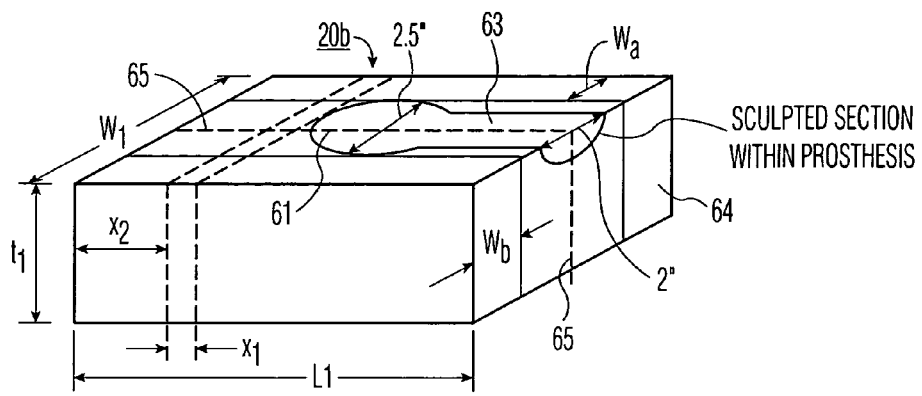
FIGS. 6A, 6B and 6C are simplified diagrams of a cushion prosthesis embodying the invention for the heel of a person.

FIG. 6A shows a top view of a simplified representation of a cushion/pad prosthesis 20b embodying the invention. The article 20b is formed of a rectangular piece of foam having a length, L1, a width, W1, and a thickness, t1. The article 20b is symmetrical about a central axis 65 running along the length of the article between the two outer sides. Along the center axis, near one end 62 of the article, there is a circular conic-like, semicircular, or elliptical cutout 61 which is sufficiently large to enable a user to place his/her heel into the cutout. The cutout may be shaped to fit the user's foot, either exactly or approximately. Where the material with which the pad is formed is hard, or relatively hard, it is important to shape the cutout (i.e., the inner surface of the prosthesis) to conform, more or less, exactly to the shape of the user's foot. Where the material is soft, it is not so important because the softer material may have sufficient deformability ("give") at low pressures to provide good contouring for the foot without introducing a significant back pressure. Extending from cutout, 61, to the end 64 of the article there is a semi-cylindrical, tubular cutout 63 for the placement therein of the ankle and lower leg region of the user, as shown in FIG. 6C. The cut outs 61 and 63 would leave a profile of the type shown in FIG. 6B and the foot of a user would rest within the prosthesis as shown in FIG. 6C.

Figure 6B:
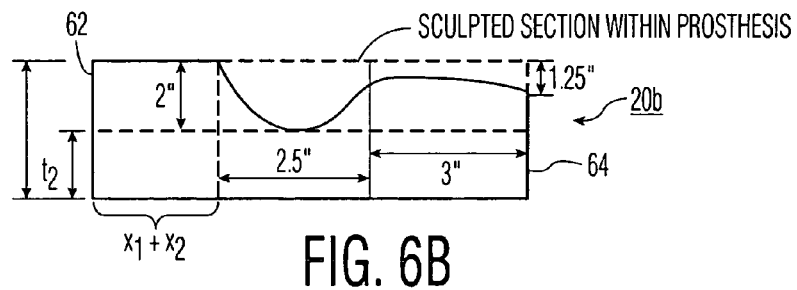
Figure 6C:
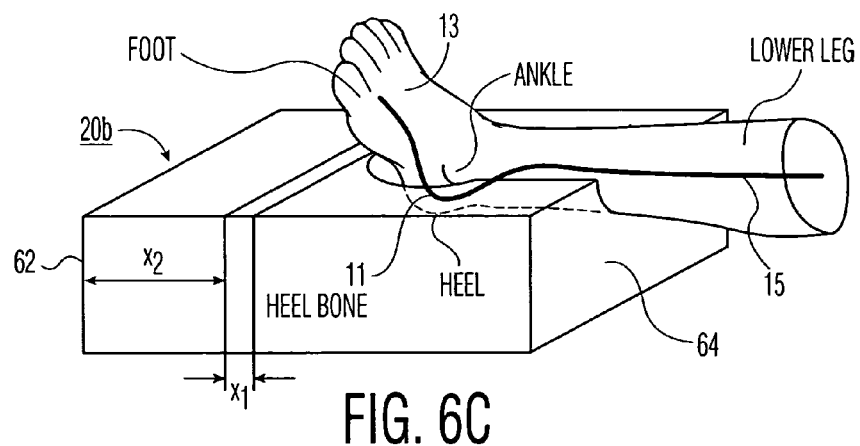

A rectangular prosthesis with a sculpted section in accordance with FIGS. 6A, 6B and 6C was made using a mushy foam (i.e., a foam having a stiffness modulus of 12 psi and a density of 1.1 lbs/ft.sup.3) with a length, L1, of 8 inches, a width, W1, of 6.5 inches and a thickness, t1, of 3 inches. As shown in FIGS. 6A, 6B, 6C, the cutout for the heel region was approximately 2.5 inches in diameter and the semi-cylindrical cutout for the leg region had a width of approximately 2 inches. The depth of the cutouts ranged from 2 inches to 1.25 inches. For this prosthesis, the pressure measured at the bone-soft tissue interface was equal to 2.7 millimeters of Hg. It is believed that this pressure level is so low that it will prevent the development of any pressure ulcer at the heel/ankle region and/or will enable any existing pressure ulcer at the heel/ankle region to be cured, regardless of the physical condition of the user.

For the comfort of the user the dimensions of the prosthesis may be changed. For example, in one embodiment, the portion X1+X2 of the cushion 20b (shown in FIGS. 6A-6C) extending beyond the bottom of the foot was reduced from 2 inches to an X1 of less than one inch. Likewise, the width W1 of the cushion was reduced (i.e., Wa and Wb were decreased) from 6.5 inches to less than 4.5 inches. Similarly, the thickness of the cushion was reduced to less than 3 inches.

The cutout and height of the cushion may be such as to cover the ankle, whereby if, and when, the user turns on a side, the padding will protect the soft tissue underlying the ankle bone area. Thus, protection for the ankle area is obtained while providing a comfortable soft layer between the ankle area of either one or both of the user's feet and any support surface.

Applicants' invention is directed to means for redistributing the weight over as large an area as possible. Thus in accordance with the invention the heel region is not made to float free which would transfer the weight of the body part to another point or region of the body. Rather, in accordance with applicants' invention the weight of a body part is distributed via a protective device which covers the entire surface area and volume of the body part being protected. In particular, the high pressure areas of the body (e.g., 11 to 21 of the heel, as shown in the various figures) are designed to make contact over an extended surface area with the prosthesis which distributes the weight and reduces the pressure in, and at, that region. Any prosthesis embodying the invention may be formed by using a mesh or mesh-like material so long as this material provides good contact to the surface area to be protected and is effective in distributing the overlying weight. In some instances, a mesh-like material may be beneficial in enabling the skin and any dressing to "breathe".

Figure 6D:
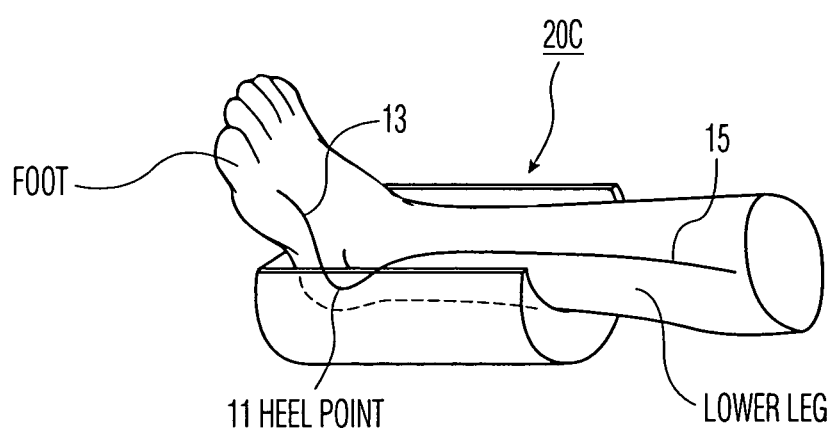
FIGS. 6D and 6E are simplified diagrams of a cylindrical cushion prosthesis embodying the invention for the heel and ankle of a person.
Figure 6E:
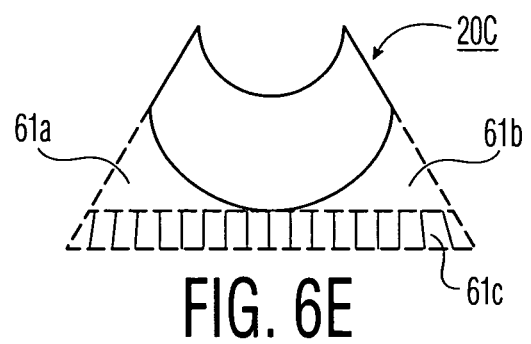

Instead of a rectangular cushion, a prosthesis 20c may be formed having a cylindrical shape as shown in FIG. 6D. The cylindrical shape of the prosthesis of FIG. 6D may be modified as shown in FIG. 6E to include sections 61a and 61b which would function to stabilize the position of the foot while providing additional weight distribution along the sides of the foot, ankle, heel and leg. Still further, the prosthesis 20c may include an additional section 61c to make the protective device thicker. Increasing the thickness may be appropriate to provide greater pressure relief if needed by the user. This additional section could be made part of the original device or may be attached thereto in any suitable manner.

Another aspect of the invention is the recognition that where the prosthesis is made of a soft material, the firmness of the support surface on which the foot (or other body part) rests affects the weight distribution. That is, the recognition that the entire system to be considered extends from the bony point (seeing the greatest weight concentration) to and through the prosthesis and to and through the support surface. All these considerations may be factored in the design and prescribing of a prosthesis for any particular individual.

When using a soft-mushy prosthesis, the thickness and softness of the soft tissue and the prosthesis material between the bony prominence and the skin mattress interface affects the actual pressure experienced by the soft tissue at the bony prominence. In fact, the size (volume) of the protective device as well as the material out of which it is formed are significant.

Figure 13A:
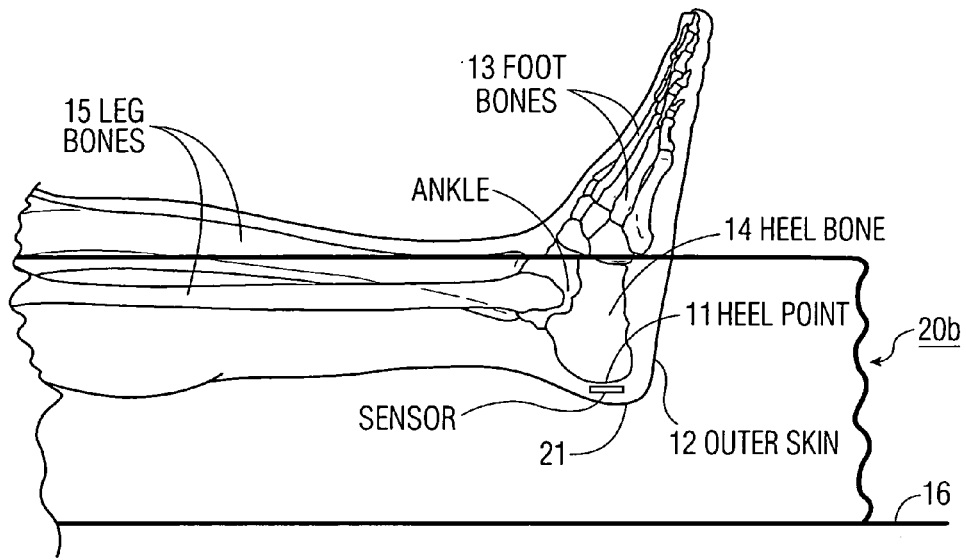
FIG. 13A is a diagram of the leg and foot of a mannequin with a pressure sensor mounted at the interface between the bony prominence 11 and the underlying soft tissue layers.
Figure 13B:
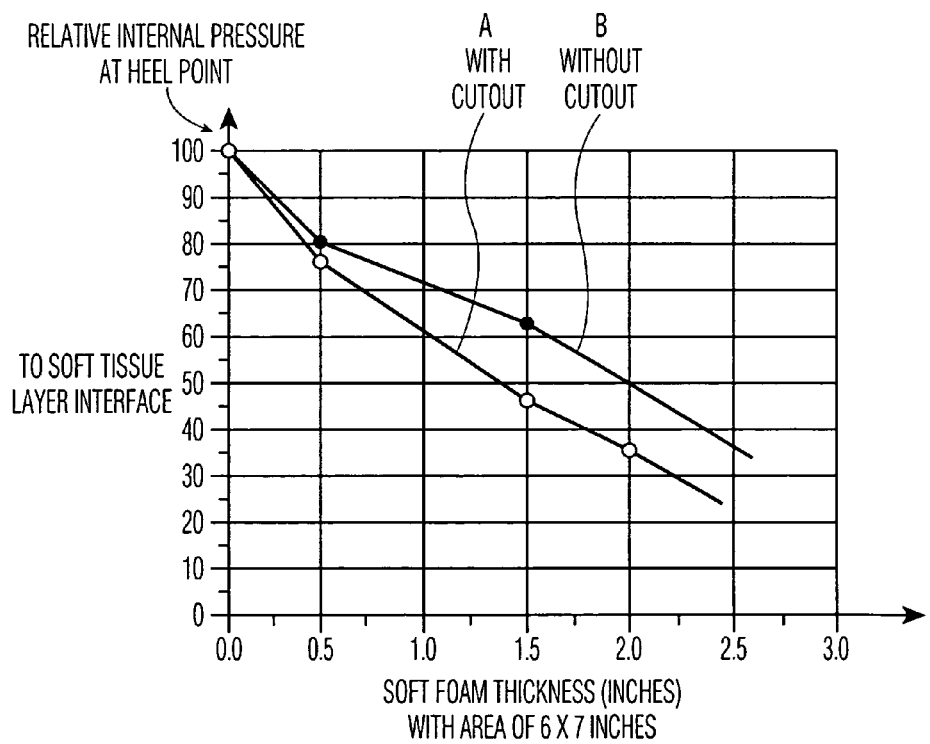
FIG. 13B is a graph showing the pressure developed at the interface between the heel bone and the underlying soft tissue as a function of the thickness of a prosthesis placed underneath the heel.

Applicants recognized that the thickness of the protective device may be varied (i.e., increased) to decrease the pressure at the bone-soft tissue interface. This may be illustrated by reference to FIG. 13B, which is a graph of the pressure at the bone-soft tissue interface as a function of the thickness of a protective device placed between the heel/ankle and the supporting surface 16. The results shown in FIG. 13B were obtained by sensing the pressure at the heel point (see FIG. 13A) of a mannequin whose foot was placed on top and/or within a prosthesis of the type shown in FIGS. 6A-6C. Measurements were taken with the leg/foot/heel positioned on top of a mushy foam layer without any cutout and then positioned on top of the mushy foam layer with a cutout for the heel/leg. Applicants demonstrated that increasing the thickness of a soft prosthesis decreases the pressure sensed at the heel point. Applicants also demonstrated that making the inner surface of the device conform more closely to the shape of the body part further increases the effectiveness of the protective device in reducing the pressure at the bone-soft tissue interface. For the testing resulting in the graph of FIG. 13B, a pad having a length of 7 inches and a width of 6 inches was used. For the cutout, a 2 inch diameter circle hole was sculpted out of the padding to a depth of approximately 0.5 inch. The particular material used for these tests was a mushy foam having a stiffness modulus of 12 psi and a density of 1.1 lb/ft.sup.3. FIG. 13B illustrates results when the thickness of the prosthesis had a cutout and when there was no cutout. The cutout simulates a condition of greater conformability between the prosthesis and the body part being protected. Greater conformability decreases the amount of pressure but, as noted above, in prostheses embodying the invention, it is desirable to maintain some pressure (even though very small) to ensure intimate contact between the skin and the prosthesis and to avoid a doughnut effect. Providing a small amount of loading minimizes atrophy due to weightlessness.

Given such facts as the individual's weight, the thickness of the soft tissue layer, a prosthesis may be prescribed which will ensure that the likelihood of developing a pressure ulcer is virtually nil.

The protective device may be made in several sizes (e.g., small medium, large) and may also be made so that its thickness may be increased by attaching various layers.

Selling and Marketing of Prosthesis and Customizing Prosthesis

Prostheses embodying the invention may be made of different shapes, thicknesses and materials to accommodate different individuals. For example, as noted above, the heel region is marked by a bony prominence and a thin soft tissue layer between the bony prominence and the outer skin layer. This renders the region subject to pressure ulcers. However, some individuals may have a very thin soft tissue layer at that point rendering them even more susceptible. For these individuals the prosthesis would have to be made thicker. It is within the ambit of the invention to measure, or sense (preferably non-invasively, but if needed, invasively) and determine the "thinness" of the soft tissue layer in order to select and prescribe the prosthesis best suited for the person's body part (e.g., the heel) in order to heal an existing pressure ulcer or to prevent the development of one. Equipment to measure the thickness and or thinness of the soft tissue layers underlying a bony prominence of the various body parts may include, for example, X-rays, CAT scans, MRIs, ultrasound or any other suitable diagnostic tool.

Trochanter

Figure 7A:
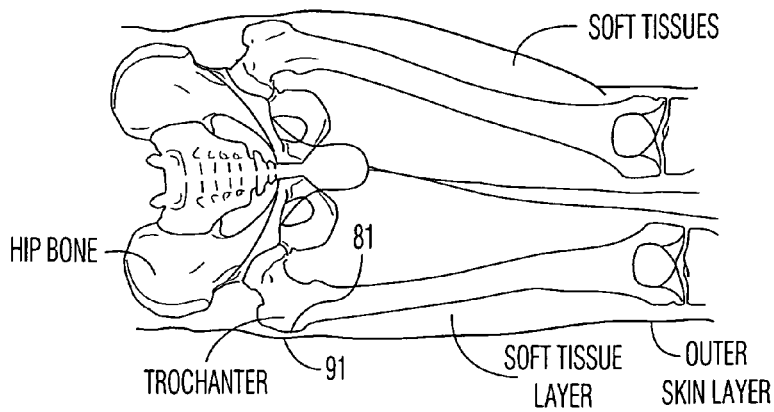
FIGS. 7A, 7B, 7C and 7D are various views showing the position of the trochanter and the surrounding soft tissue area to illustrate the problem of the weight exerted on the soft tissue layer below the trochanter when an individual is lying on his/her side on top of a support surface and the resulting pressure cone.
Figure 7B:
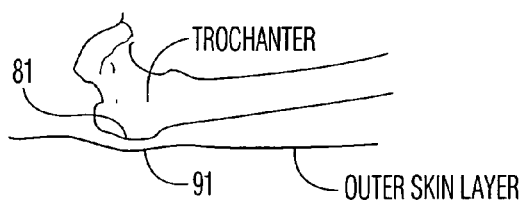
Figure 7C:
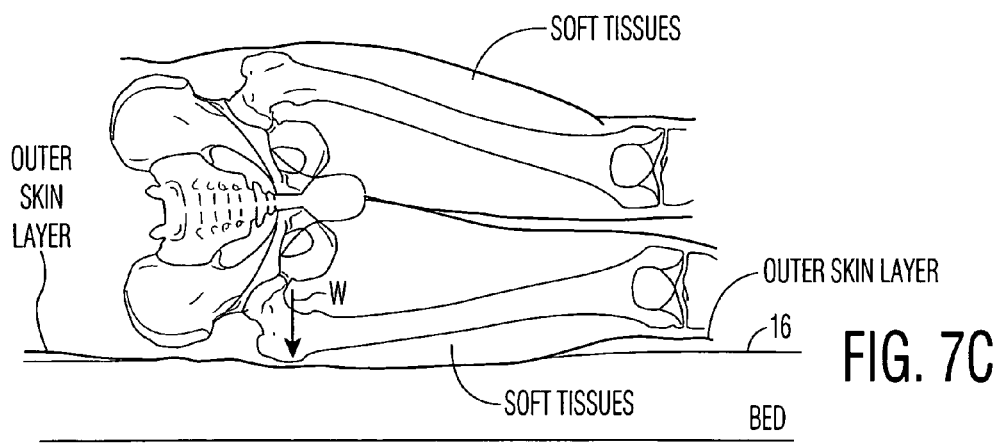
Figure 7D:
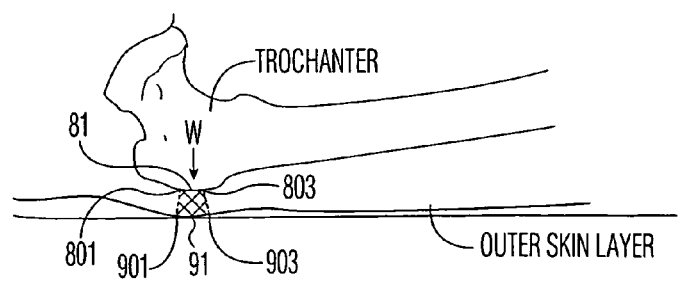

FIG. 7A is a top view of the skeletal structure showing the bony prominence 81 of the trochanter and the relatively thin soft tissue layer between the bony point 81 and the corresponding outer skin layer 91. FIG. 7B is a blow up of the trochanter region to illustrate the bony prominence of the trochanter and the thinness of the underlying soft tissue region. FIG. 7C illustrates what occurs at the trochanter region when an individual lies on his/her side on top of a support surface, the weight of the body overlying the trochanter is concentrated to a great extent over a small region abutting the bony prominence 81. Consequently, as shown in FIG. 7D, a significant weight, W, is applied to a small region 81 (arc 801 to 803) and the weight is exerted over a small "pressure cone" like region (shown hatched in FIG. 7D) having a diameter at the surface 16 extending from point 901 to 903.

Figure 7E:
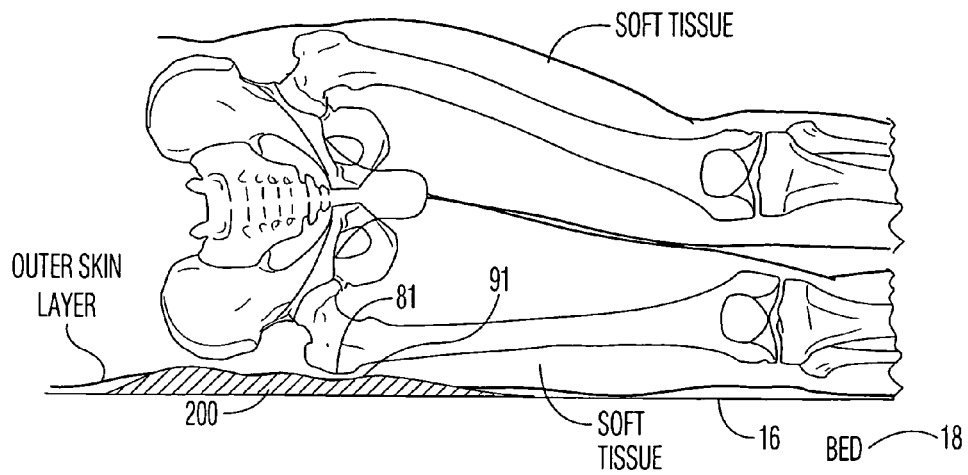
FIGS. 7E, 7F, 7G are various views of a protective device embodying the invention suitable for use with the trochanter area of a body.

FIG. 7E illustrates the placement of a prosthesis 200 between the trochanter region and a support surface 16. The protective device 200 functions to distribute the weight over a much larger area and volume as schematically illustrated in FIG. 7H. Note that the weight W is now effectively distributed over a much larger region as denoted by arc 811 to 813 in region 81 at the interface between the bony prominence 81 and the underlying soft tissue layer. With prosthesis 200 in place, the overlying weight is distributed over a much larger region (as denoted by arc 911 to 913) at the interface between the outer skin layer and the interface with the protective device 200. Still further, the protective device enables the weight to be distributed over a still greater region as denoted by length 211 to 213 at the interface of the protective device 200 with the support surface 16. For purpose of illustration the "pressure cone" subtending the full weight in the absence of the protective device is shown as a hatched cone having a final diameter d1, in FIG. 7H.

Figure 7F:
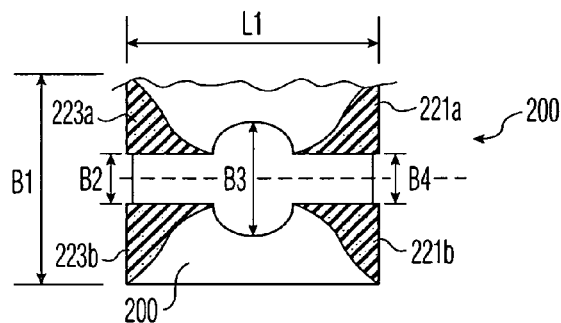
Figure 7G:
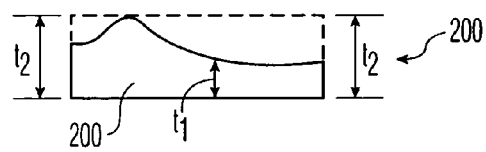
Figure 7H:
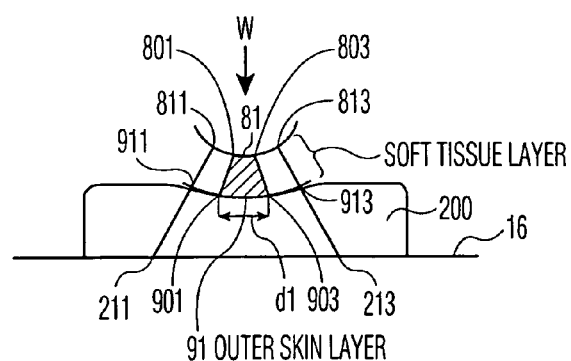
FIG. 7H is an idealized representation of weight distribution at the trochanter region of an individual resting on his/her side on a support surface using a prosthesis embodying the invention.

A protective device or prosthesis 200, suitable for the trochanter area may be a soft material sculpted pad as shown in FIGS. 7F and 7G. The device 200 is shown to have a width B1, a length L1, and a thickness t2; where the range of the width, B1, can vary from within, or at, the dimensional envelope of the actual trochanter to the full side width, or more, of the user; and where the range of the length, L1, can vary from within, or at, the dimensional envelope of the actual trochanter to the full side length of the user. The thickness t2 may be varied to provide the desired pressure relief. The protective device 200 may include a pad having a central cut out of general diameter B3 shaped to enable the trochanter (and possibly the hip) area to be comfortably placed therein, with the thickness of the pad being sufficient to decrease the pressure to a desirable level. The protective device 200 may include cutouts 221a, 221b along the leg or upper thigh region. Likewise, the protective device 200 may include cutouts 223a, 223b for the hip region.

The protective device 200 may be attached to the body in several different ways. In one embodiment a prosthesis 200 may be attached around each leg or thigh by straps or meshing or adhesive akin to the showing of FIGS. 5A-5C. Alternatively a prosthesis 200 for each side of the body, or for both sides, could be secured by means of a belt like strap going around the body.

Figure 7I:
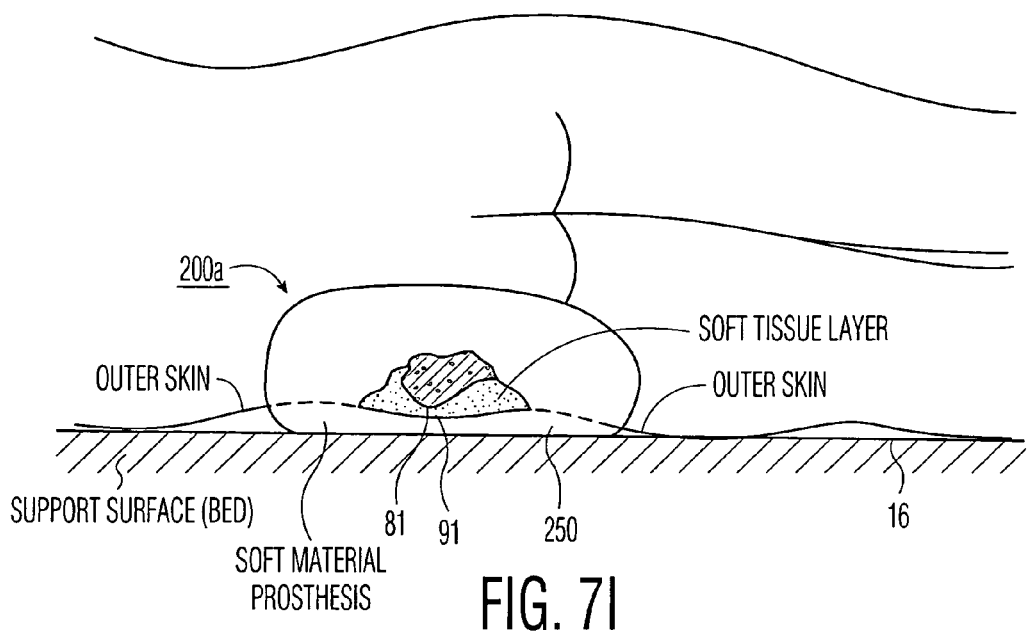
FIG. 7I is a cutaway cross sectional view of a prosthesis placed underneath the trochanter of an individual lying on his/her side.
Figure 7K:
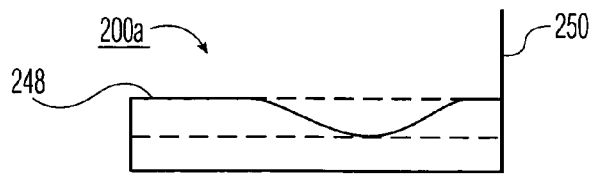
FIGS. 7J and 7K are, respectively, perspective a view of the inner surface of a soft prosthesis and a cross sectional elevation of that prosthesis for application to a trochanter.
Figure 7J:
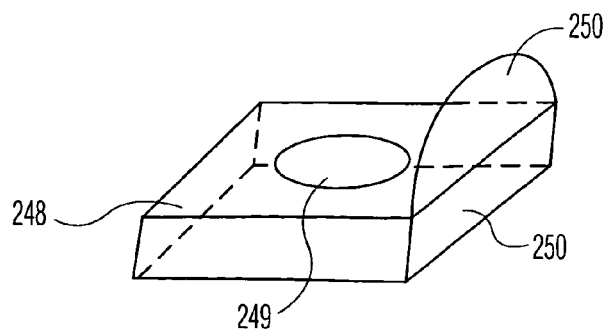
Figure 7L:
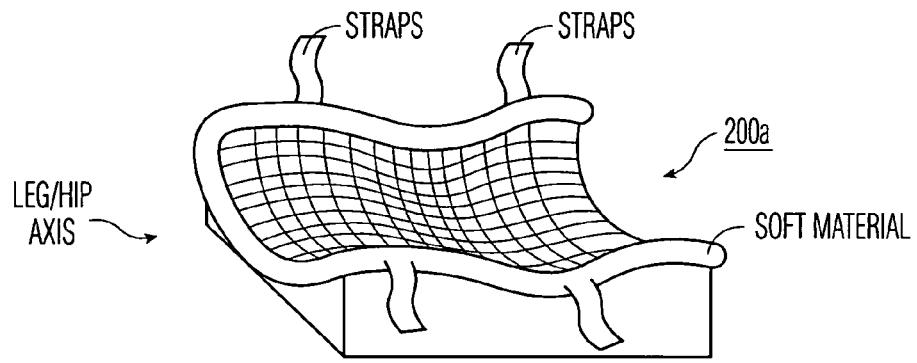
FIG. 7L is a perspective view of another prosthesis suitable for application to a trochanter.
Figure 7M:
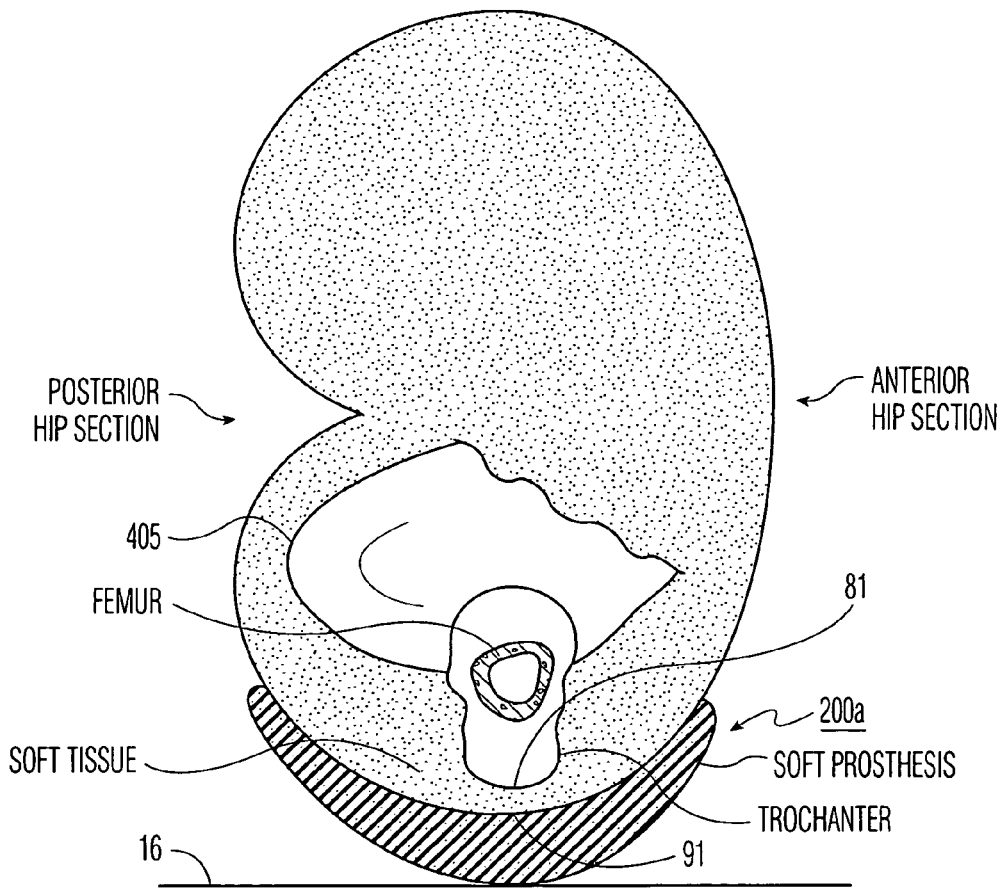
FIG. 7M is a cross section of a prosthesis suitable for application to a trochanter.

FIG. 7I shows a cutaway view of the trochanter highlighting the bony prominence 81 and the thin soft tissue layer between bony point 81 and corresponding skin layer 91. FIG. 7I also shows a rear view of a soft material prosthesis 200a extending underneath the trochanter region of a body lying on its side and extending around the back. The protective device 200a would extend underneath the body, as discussed above, to reduce the pressure at the interface between the bony prominence 81 and the soft tissue layer and across the soft tissue layer, the outer skin and at the interface between the outer skin and the prosthesis 200a. As shown in FIGS. 7J and 7K which are simplified views of the prosthesis 200a, the lateral portion 248 of the prosthesis 200a, intended to be placed below the trochanter region, may extend for the full length and width of the hip section of the body, or only for a small section under the trochanter; while the upright section 250 extending above the horizontal may extend partly or wholly around the body part. The prosthesis may include a recessed region 249. The inner surface of the prosthesis 200a may be shaped to conform to the shape of the trochanter and hip area as shown in perspective in FIG. 7L. As noted above, where the prosthesis is formed of a soft material a degree of conformance is helpful, but not necessary, to achieve pressure relief. The prosthesis may be made with straps for attachment to the body. As shown in FIG. 7M the prosthesis may wrap symmetrically around the trochanter region of the body.

In the prosthesis for the foot, the thickness of the active area of pressure redistribution of the prosthesis may vary in several ways. The thickness in the region where the pressure from the bony prominence is being distributed will vary inversely with the thickness of the skin and underlying soft tissues of the person (patient). Therefore, if the soft tissue is very thin, the thickness of the prosthesis will be greater than if the soft tissue is thick. For estimation purposes only, at this site the prosthesis may be as thin as 1 mm and as thick as 100 mm. The thickness in the region where the pressure from the bony prominence is being distributed will vary directly with the actual pressure load to be distributed (PLD). Therefore, if the PLD is very high, the thickness of the prosthesis will be greater than if the PLD is low. For estimation purposes only, at this site the prosthesis may be as thin as 1 mm and as thick as 100 mm.

The thickness of the prosthesis in the region of the body surrounding the active area of pressure re-distribution is designed to provide a comfortable structure for the patient without compromising the pressure re-distribution function of the active area. A tapering means may be employed to gradually bring the prosthesis structure from the thickness of the active area to being flush with the skin surface of the patient. FIGS. 2A, 3A, 4, 7E, 7F, 7G show a prosthesis construction based on this concept.

Where multiple points must be protected, such as the heel and the ankles of the foot (or for the trochanter and hip areas), the active areas may overlap. In that case, there may be a direct change in thickness over one active area with no surrounding areas in between. Then, any gradual thickness change would occur on the areas surrounding all the active areas in question. Again, this is generally shown in FIGS. 2A, 3A, 4 and 7E-7G.

A soft prosthesis embodying the invention may be formed of any material which enables the re-distribution of the overlying weight. By way of example, materials from which the "soft" prostheses, discussed above and the ones to be discussed below, may be constructed include, but are not limited to, open-cell foams, closed-cell foams, gels, soft elastomeric non-foam polymers and fleeces. Also included are constructions using more than one material. This latter is likely to be the case where the prosthesis is combined with a wound dressing to provide the pressure re-distribution performance with a healing environment to allow a pre-existing pressure ulcer to heal or to prevent skin damage from factors other than pressure (such as moisture, shear, friction, heat, and incontinence) which can exacerbate the problem by weakening the skin and allowing ulcers to form more readily because of the compromised condition of the skin.

Ischium

Figure 8C:
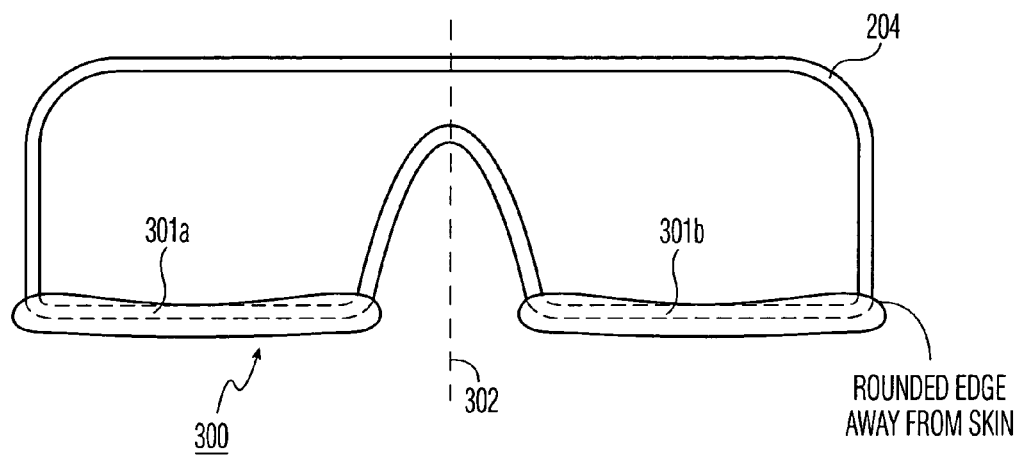
FIGS. 8C and 8D are, respectively, a rear view and a perspective view of a soft material prosthesis embodying the invention.
Figure 8D:
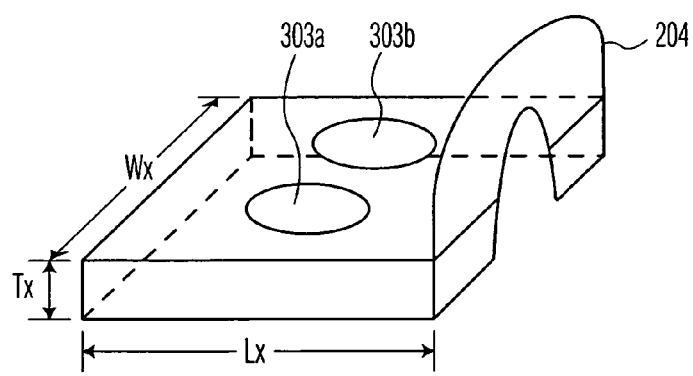
Figure 8E:
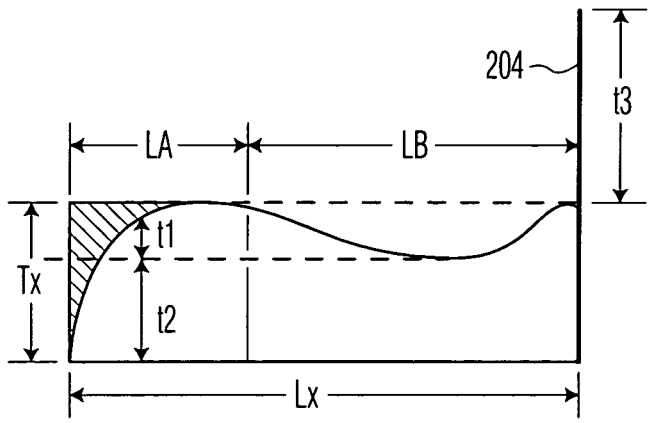
FIGS. 8E and 8F are simplified and idealized elevation and perspective drawings, respectively, of a prosthesis suitable for application to the ischial regions.
Figure 8F:
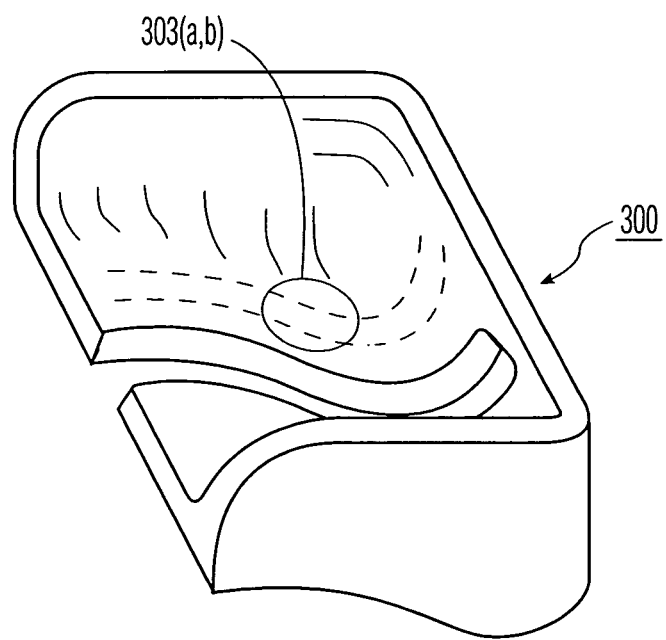

FIG. 8A includes a rear view and FIG. 8B includes a cross sectional view of a person sitting on a protective device 300 made of a soft material (e.g., a "mushy foam"). These figures include a cut away of the ischium of the sitting person. The bony prominence region 181 of the ischium overlies a soft tissue layer resting on an outer skin portion 191 which rests on a layer 301a of device 300; where the layer 301a rests on a support surface (e.g., chair or bed). As shown in FIG. 8C, the prosthesis may be symmetrical about a central axis 302, each side (301a, 301b) of the prosthesis being designed to carry its respective body part. As shown in FIG. 8D, the prosthesis includes a portion extending for a predetermined length Lx, with a width Wx and a thickness Tx with recesses 303a, 303b conforming generally to the shape of the ischium. FIG. 8E is an elevation diagram of the prosthesis. FIG. 8F is a perspective view of a single piece prosthesis using a soft material for simultaneously protecting the left and right ischial regions. Note region 303(a, b) may be recessed to conform to the extension of the ischium while being thick enough to provide good weight distribution. Consequently, the pressure at the interface between the ischium and its corresponding soft tissue layer may be maintained below a predetermined level. The protective device shown in FIGS. 8C-8F includes a back and side portion. It should be noted that, instead, a much simpler structure comprising a circular or elliptical pad of sufficient thickness could be attached below each ischium to provide the desired pressure relief.

Coccyx

Figure 9A:
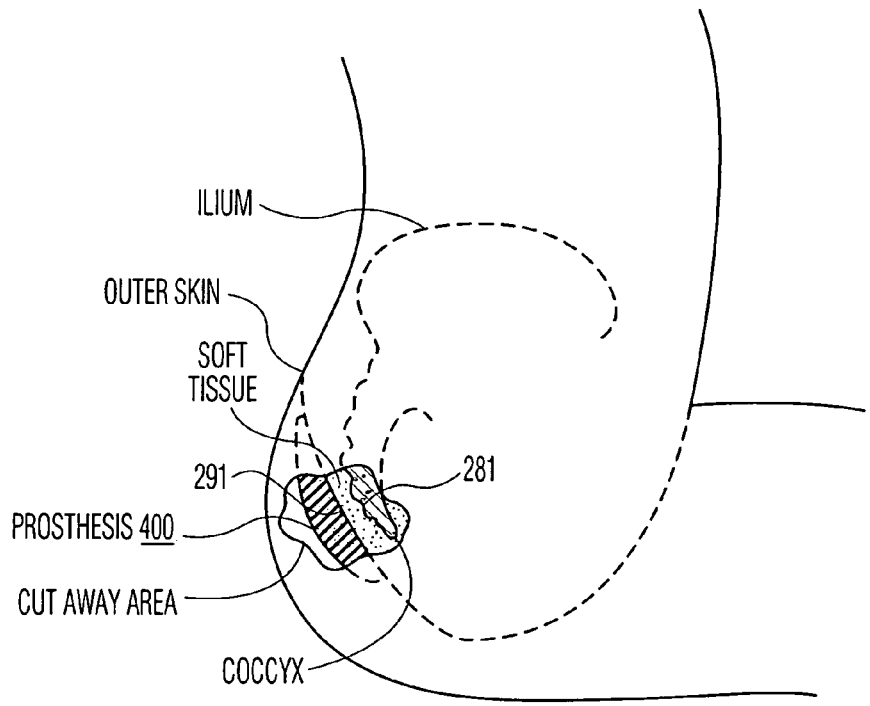
FIG. 9A is a cutaway view of the coccyx and a cross section of a prosthesis for protecting the area from excessive pressure.
Figure 9B:
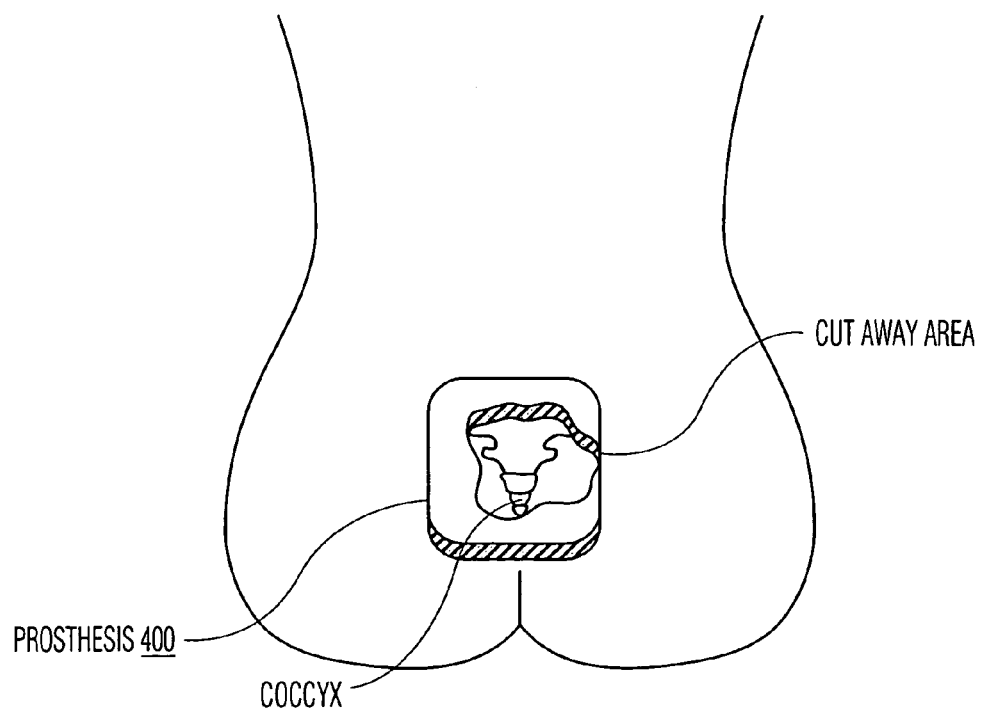
FIG. 9B is a rear view of the coccyx with a prosthesis attached thereto.

FIG. 9A is a cross-sectional cut away view and FIG. 9B is a rear view of the coccyx region showing the bony prominence 281, the adjoining soft tissue layer and the corresponding outer skin region 291. A soft material protective pad 400 may be attached to the outer skin region to reduce the pressure at the bony prominence-soft tissue interface and across the soft tissue layer to less than a predetermined level.

Sacrum

Figure 9C:
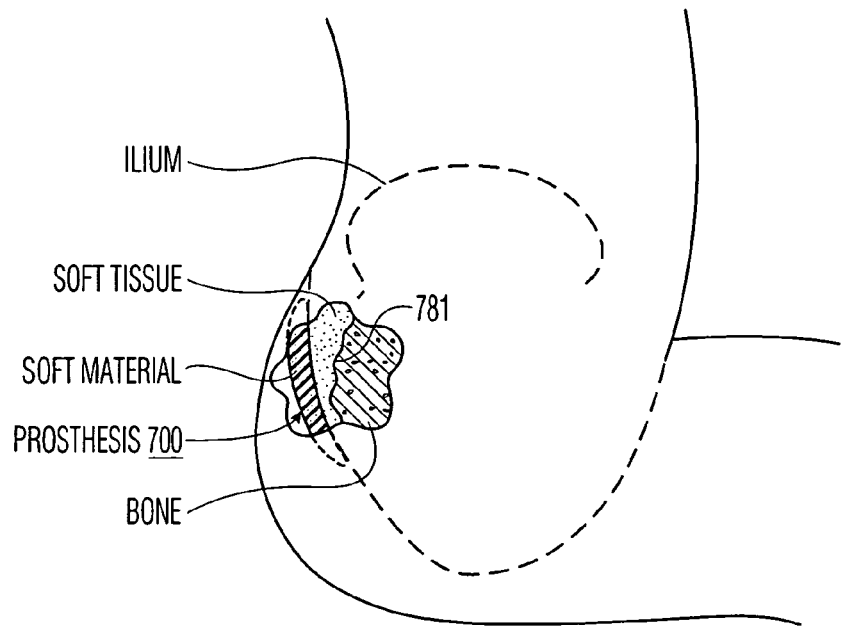
FIGS. 9C and 9D are cut away/cross sectional views of the sacrum and a cross sectional view of a soft prosthesis attached thereto.
Figure 9D:
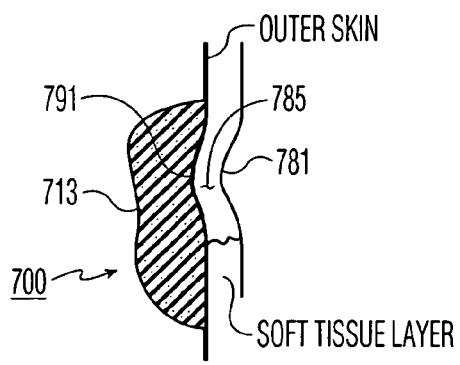
Figure 9E:
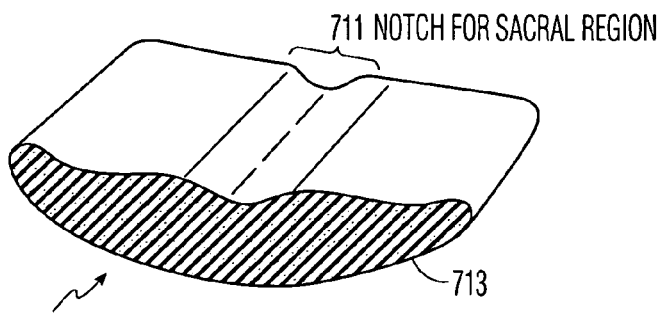
FIG. 9E is a simplified perspective view of the prosthesis of FIG. 9C.

FIG. 9C is a cross sectional cut away view of a sacrum region showing the application of a "soft" prosthesis 700. A blow up of the sacrum region is shown in FIG. 9D illustrating a bony prominence 781, an intervening soft tissue layer 785, and a corresponding outer skin layer with contact area 791. FIG. 9E is a perspective view of the soft prosthesis 700 with a notch 711 for conforming to the sacral region. The prosthesis 700 may be attached in many ways, discussed above and below.

The protection for the sacrum differs somewhat from the protection needed at other body sites in that a shear component, as well as the pressure component can play a part on the loading at the bony prominence 781 soft tissue 785 interface and at the soft tissue to outer skin 791 interface. This is especially so when the upper part of the person's body is elevated on a bed or reclining chair. There is a shear vector at the sacrum region due to forces tending to push the body down, as well as a compression force due to the weight of the body pushing the skeletal structure against the bed or chair. The shear vector acts at 90 degrees to the compression (pressure) vector. Therefore, the resultant force is at an angle between the shear and compression. The compression vector and its reduction would be treated by the prosthesis in a similar manner as for the other sites. The shear vector and its reduction are treated by allowing the external surface 713 of the prosthesis to deform, or otherwise reduce, the shear loading on the soft tissues and allow the friction load to be dissipated at the external surface 13. The shear vector may be distributed more effectively with a prosthetic material at its outer surface 713 having some elastomeric or viscoelastic elastic behavior allowing the prosthesis to deform rather than the outer skin and the soft tissue layer.

Scapulae

Figure 10A:
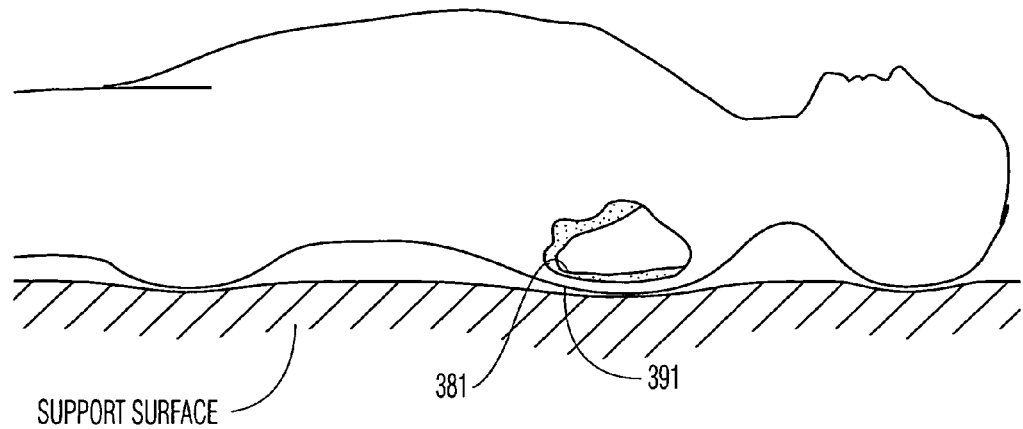
FIG. 10A is a cross sectional cutaway view of a scapula region.
Figure 10B:
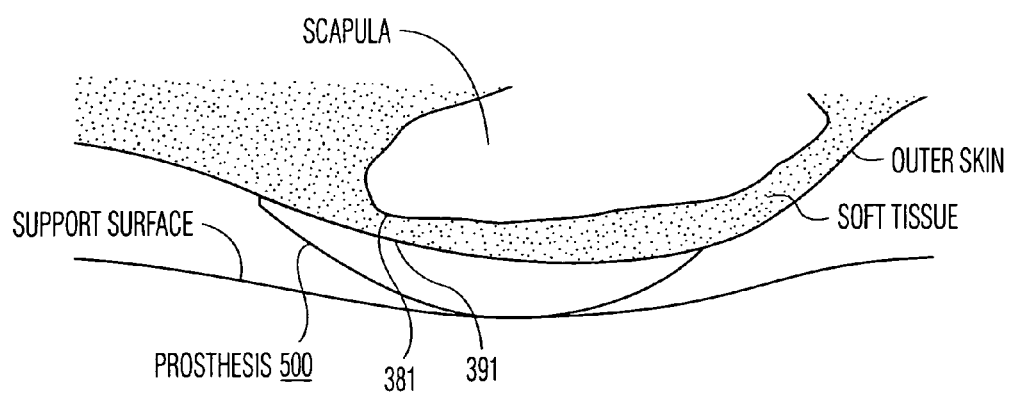
FIG. 10B is a cross sectional diagram of a prosthesis for protecting the scapula.

FIG. 10A is a cross sectional cutaway view of a scapula (shoulder bone) of an individual lying on a support surface showing the bony prominence 381 and the corresponding point 391 on the outer skin. FIG. 10B is a blowup of the scapula section showing the placement of a "soft" protective device 500 between the scapulae region and the support surface to reduce the pressure at the bony prominence-soft tissue interface and across the soft tissue layer to less than a predetermined level.

Occiput

Figure 11:
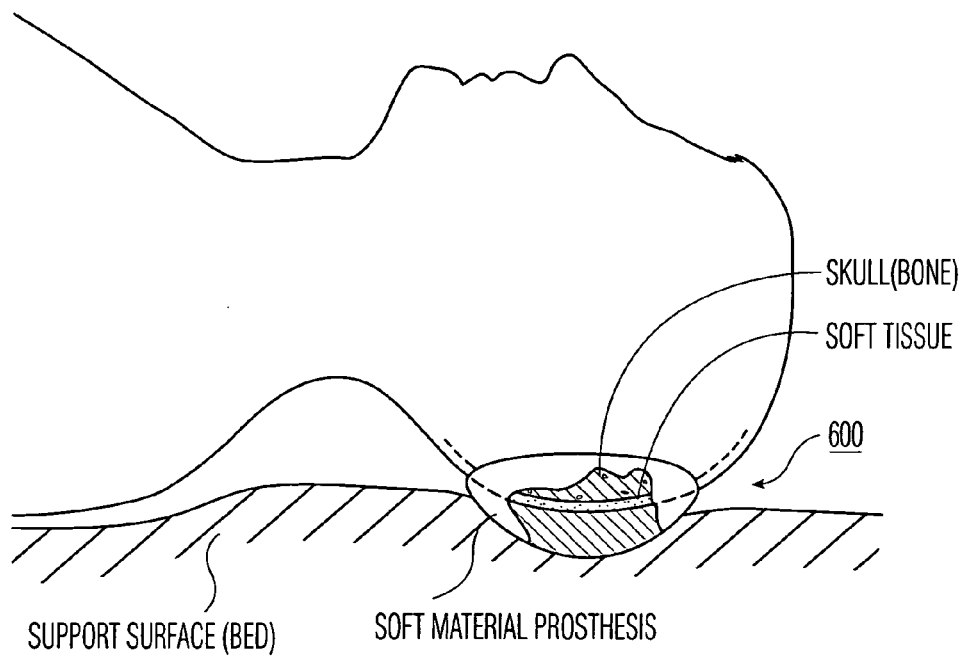
FIG. 11 is a cutaway view of the skull bone (occiput) and a cross section diagram of a soft material prosthesis protecting the occiput.

FIG. 11 is a cross sectional cutaway view of a soft material prosthesis 600 suitable for protecting the back of the head skull bone (occiput) of a user. Prosthesis 600 may be shaped like a hemisphere with a cut-out (recess) to accommodate the skull bone. The protective device may be attached to the body by a hair net, straps, an adhesive, or any other suitable attaching means.

Elbow

Figure 12:
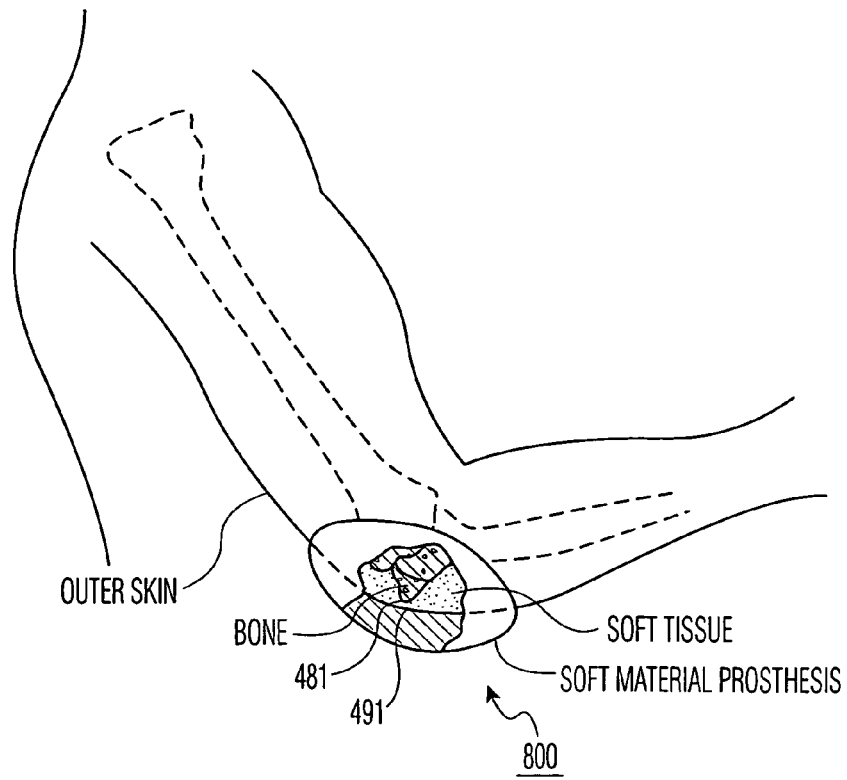
FIG. 12 is a cutaway view of an elbow and a cross sectional diagram of a prosthesis for protecting the elbow.

FIG. 12 is a cutaway view of the elbow showing the bony prominence 481, the adjoining soft tissue layer and the corresponding outer skin region 491. FIG. 12 also shows a cross sectional view of a soft material prosthesis 800 suitable for use with the elbow. The prosthesis may be banana shaped to provide support for the elbow while enabling the user to extend to extend his/her arm. This protective device may be attached to the body by straps, an adhesive, a mesh, or any other suitable attaching means.

It should be evident from the examples discussed above, that prostheses embodying Applicants' invention may be applied to reduce the pressure associated with any bony prominence or region of concern.

Hard Shell for Heel

In the description above, the prosthesis was made of soft, compliant material. Alternatively, a protective device 320 may be formed, as shown in FIGS. 14A-14D, with a "hard" shell conforming to the body part to be protected. A hard shell prosthesis isolates, to a great extent, the body part from the support surface while, if conforming, providing extensive distribution of the body weight over a large surface area.

Figure 14A:
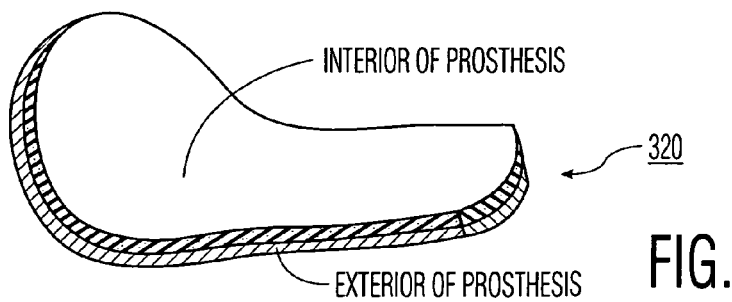
FIGS. 14A through 14D are views of a "hard" outer shell prosthesis.
Figure 14B:
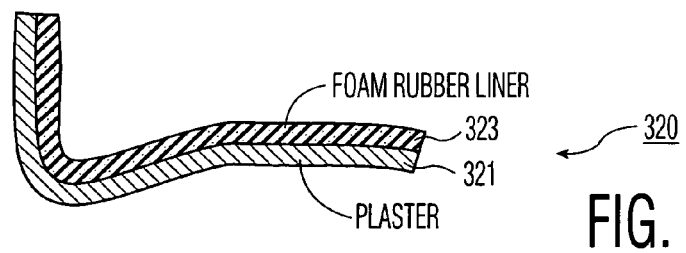
Figure 14C:
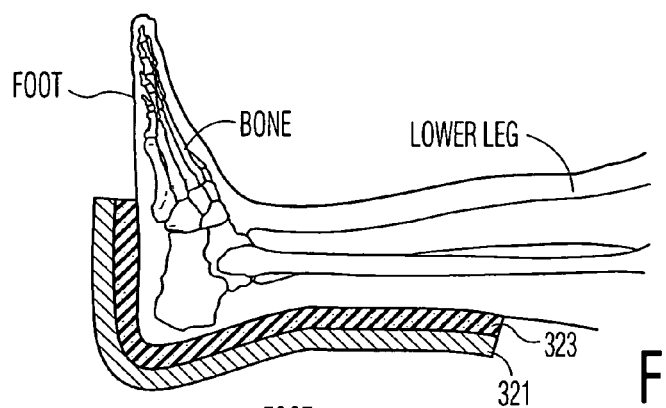
Figure 14D:
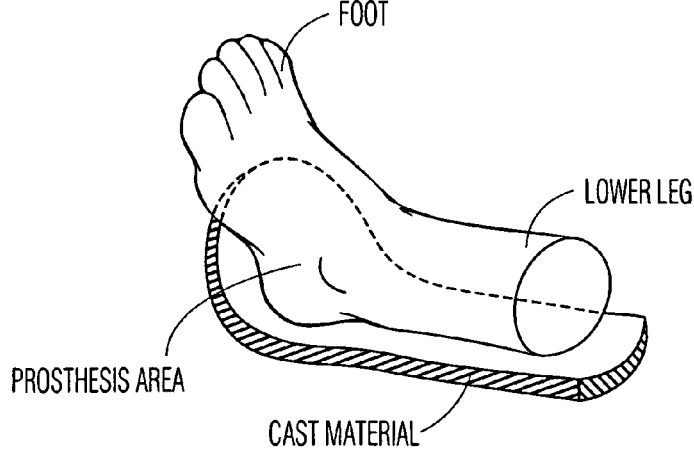

In FIGS. 14A-14D, the shell may be a plaster cast of the body part (e.g., the heel). The shell defines one layer 321 of the prosthesis and it is the inner surface of this layer 321 which is designed to conform with a high degree of fidelity to the shape of the heel (or any other body part) which it is intended to protect. A liner 323 may be formed and placed on top of the inner surface of the shell 321. The liner functions to smooth out certain parts of the "hard" shell which do not conform precisely and to provide a soft interface. The liner may be made of a "soft" substance including a soft dressing such as a hydrocolloid dressing, presently used to treat pressure ulcers. Alternatively, the liner may be made of other materials such as silicone gel, a foam, or the alginate materials used by dentists when making impressions for dentures. The prosthesis 320, with or without a liner 323, may be applied directly to a person's (patient's) skin; or over clothing (as is the case for the soft prosthesis). The prosthesis may be secured with adhesive, straps, netting, bandage wraps, dressing, or in the case of the heel, with a stocking sleeve (as is the case for the soft prosthesis). An advantage of the "hard" prosthesis is that it can be made relatively thin and less bulky and the liner, if used, can also be made relatively thin. FIG. 14C is intended to illustrate that where the prosthesis conforms to the shape of the heel and ankle the weight of the overlying body part is distributed over a large area, thus reducing the likelihood of the development of pressure ulcers.

Figure 14E:
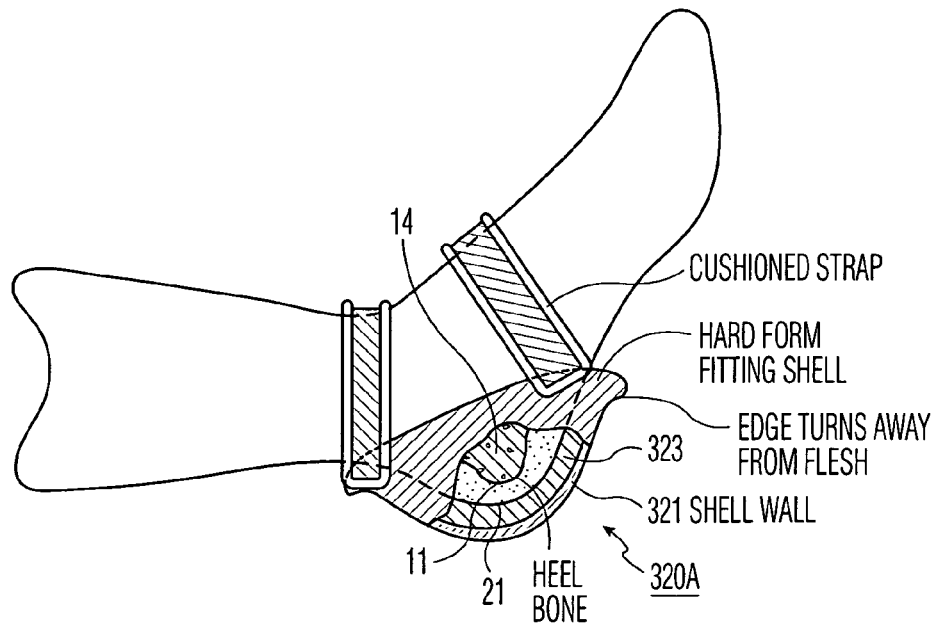
FIG. 14E is a cutaway view of the heel with a hard shell and interface material.

FIG. 14E is a perspective view of a "hard" shell prosthesis 320a mounted on a heel and a cut away view showing the heel bone 14, the heel point 11, an intervening soft tissue layer and the corresponding skin layer point 21. The inner surface of the shell wall 321 is form fitting and is made of a hard material. A liner 323 is located between the inner surface of the shell 321 and the outer skin layer. The shell may be secured to the body part by cushioned straps and the upper edge of the prosthesis would be turned away form the body.

Figure 14F:
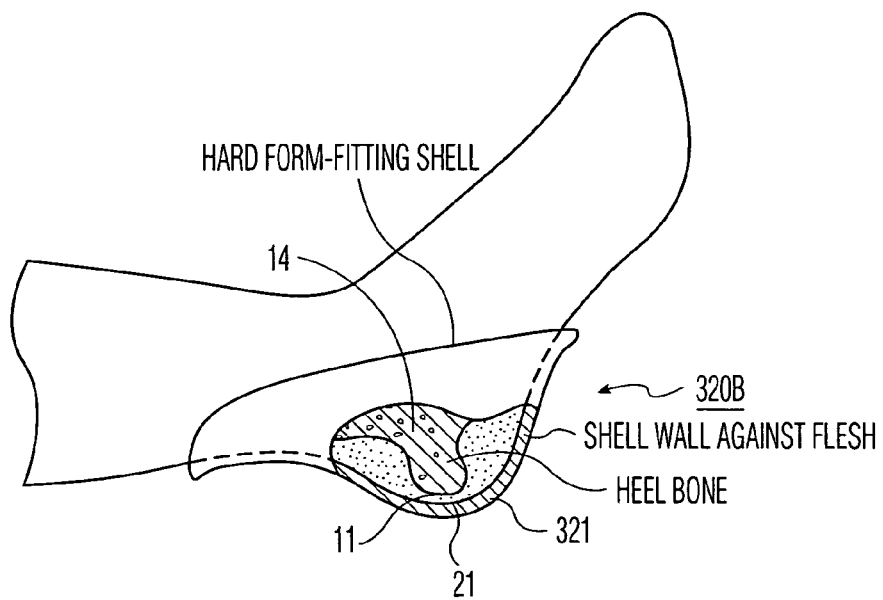
FIG. 14F is another cutaway view of the heel and a "hard" shell prosthesis.

FIG. 14F shows a hard shell prosthesis 320b mounted directly on a heel; i.e., without a liner. Prosthesis 320b may be formed like prosthesis 320a, except that a liner is not included.

FIG. 14G shows a hard shell prosthesis 320c mounted on a heel. The prosthesis of FIG. 14G may be like the ones of FIG. 14E or 14F, except that a soft outer layer 325 is formed on the outer portion of the hard shell 321 to prevent damaging other body parts with/by the hard shell prosthesis. The soft outer layer may be formed with all hard shell prostheses. The soft outer layer may also function to decrease shear and frictional forces.

Hard Shell for Trochanter

Figure 15A:
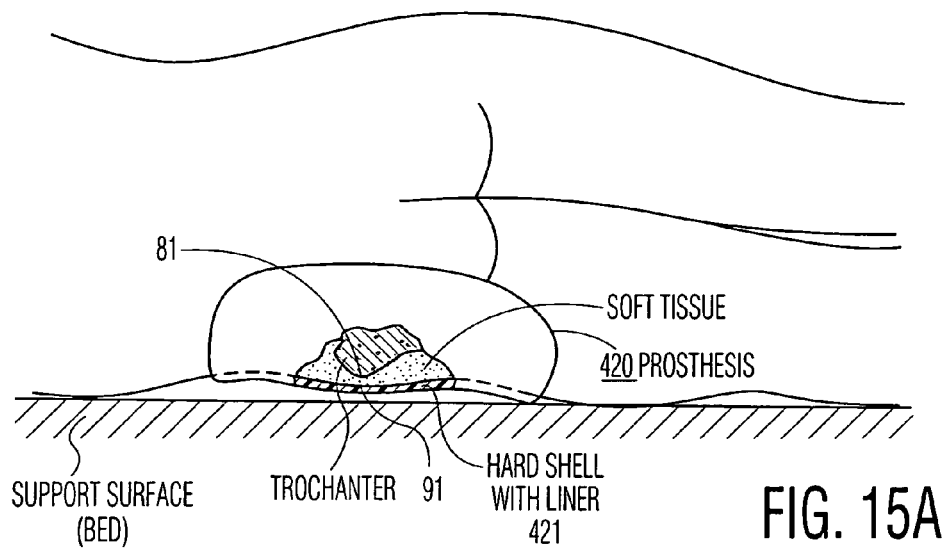
FIGS. 15A, 15B, 15C are various views of the trochanter with a "hard" shell prosthesis.

FIG. 15A shows a hard shell prosthesis 420 for use with the trochanter, whose inner surface is designed to conform with a high degree of fidelity to the overlying body part. FIG. 15A includes a cut away view of the bony prominence 81, the intervening soft tissue layer and the corresponding contact point 91. For a prosthesis with a high degree of conformance, the weight of the overlying section is distributed over a large surface area, reducing any high pressure points. As before the protective device 420 includes an outer shell 421 and may be formed with a liner 423 or have a liner attached to the inner surface of the shell 421.

Figure 15B:
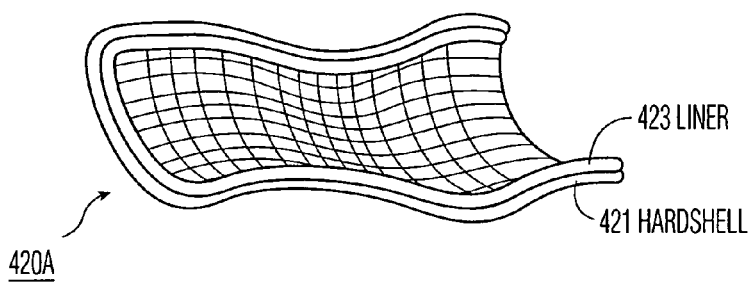

FIG. 15B is a perspective view of a hard shell prosthesis 420a shaped to conform to the trochanter and hip area of a user. A liner 423 would be used to provide better continuous contact.

Figure 15C:
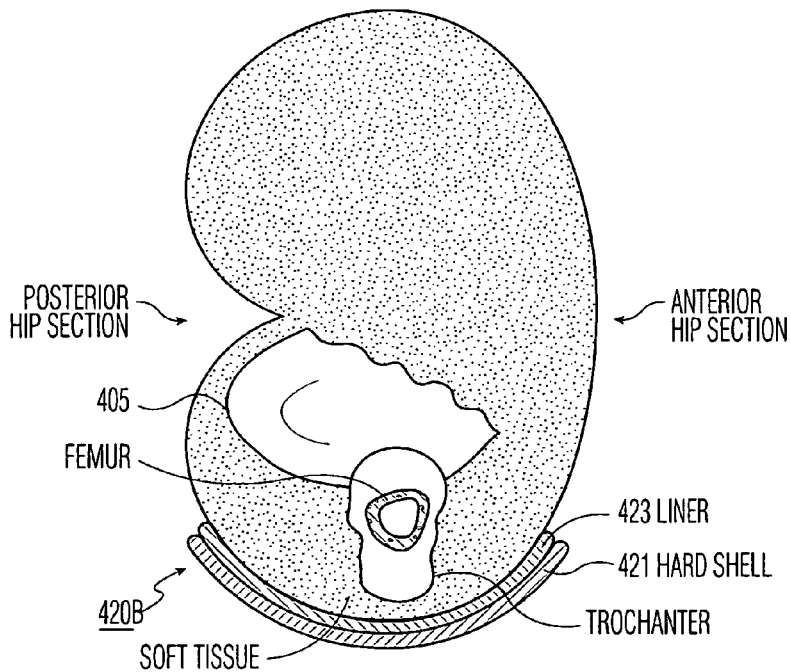

FIG. 15C is a cross sectional view of a hard shell prosthesis 420b which would extend or wrap around the hip/trochanter region. The prosthesis 420b may include a liner 423, as discussed above.

Hard Shell for Ischium

Figure 16C:
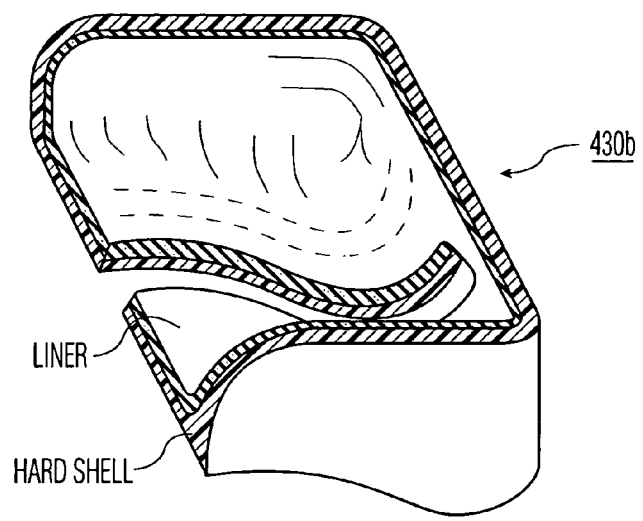
Figure 16D:
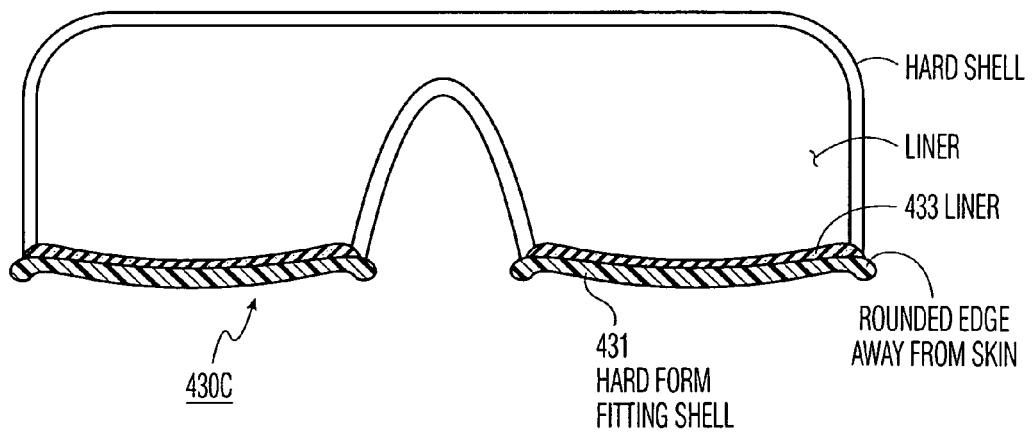

FIGS. 16A is a rear view and FIG. 16B is a cross-sectional view of a hard shell prosthesis 430 for use with the ischium of a user, shown in a sitting position. The figures also shows a cut away view of the ischium with the bony prominence 181, the intervening soft tissue layer and the contact point region 191. Where the prosthesis 430 is formed so as to conform to the contour of the body part with a high degree of fidelity, as shown in FIG. 16C, the weight distribution is spread over a large surface area. FIG. 16D is an anterior view of a hard shell prosthesis 430 highlighting that the protective device may include a hard shell 431 with a liner 433 and have a backing section so as to go around the back of the user.

Hard Shell for Coccyx

Figure 17A:
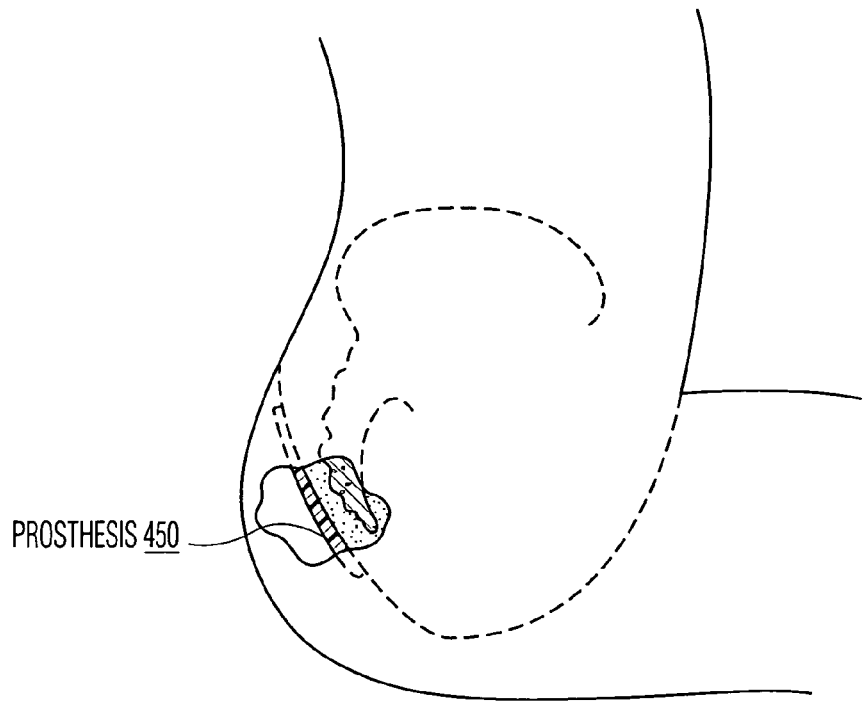
FIGS. 17A and 17B are various views of the coccyx with a "hard" shell prosthesis.
Figure 17B:
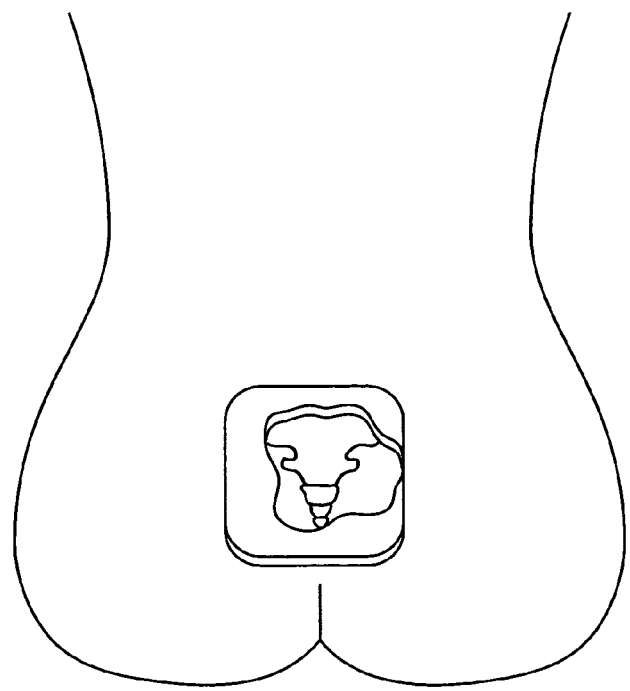

FIGS. 17A and 17B show, respectively, a cross sectional view and a rear view of the coccyx region of an individual and a hard shell prosthesis 450 with a liner attached to that area of the body.

Hard Shell for Sacrum

Figure 17C:
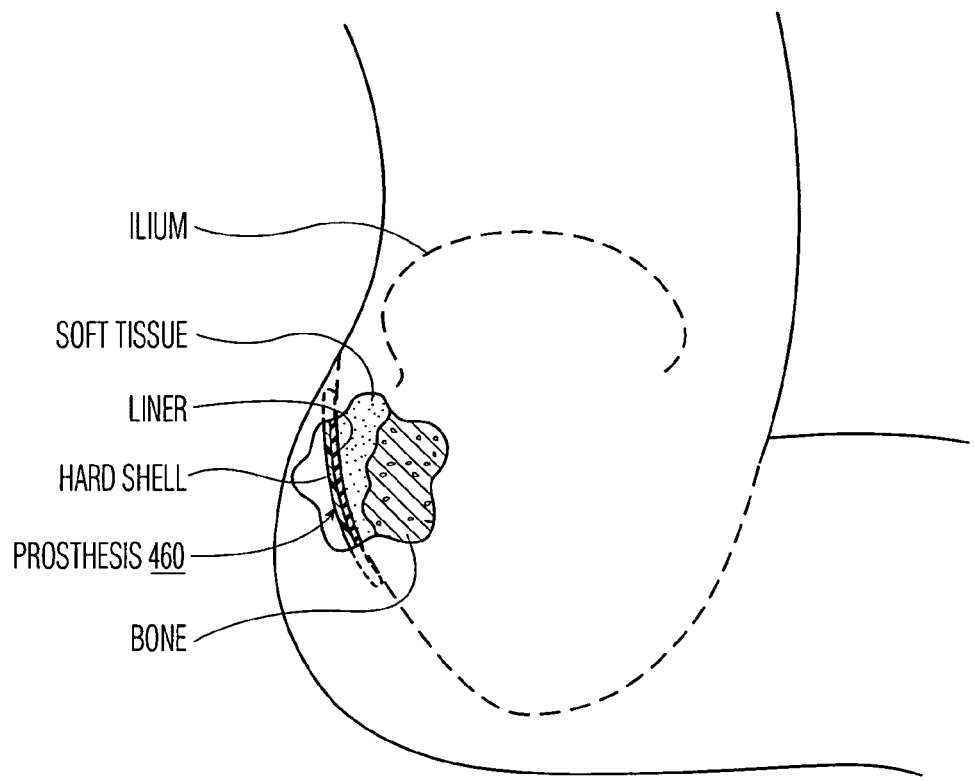
FIG. 17C is a cutaway view of the sacrum with a "hard" shell prosthesis.
Figure 17D:
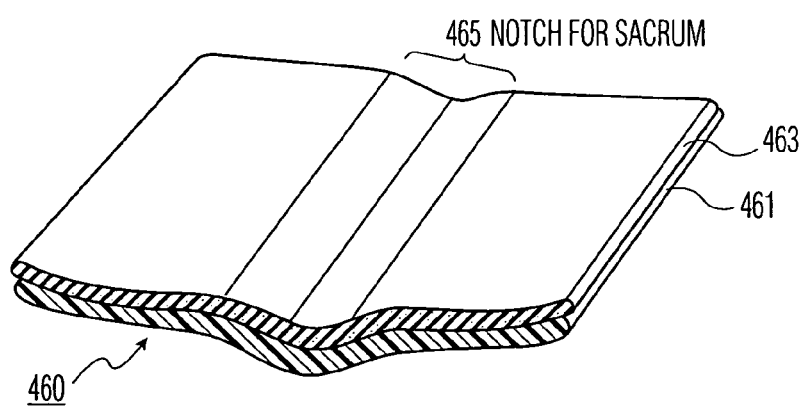
FIG. 17D is a perspective view of the prosthesis of FIG. 17C.

FIG. 17C is a cross-sectional view of the sacrum to which is applied a hard shell prosthesis 460 having an outer shell 461, an inner liner 463, and a notch 465 conforming to the sacrum, as shown in FIG. 17D. This prosthesis is also intended to protect the user against shear forces as described above for the soft prosthesis (FIGS. 9C-9E).

Hard Shell for Scapulae

Figure 18A:
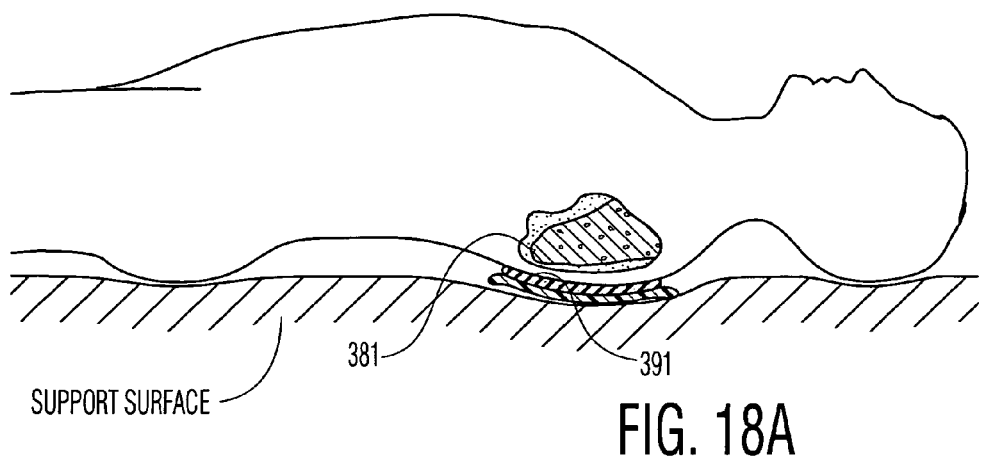
FIGS. 18A and 18B are various views of the scapula region and of a "hard" shell prosthesis for protecting that region.
Figure 18B:
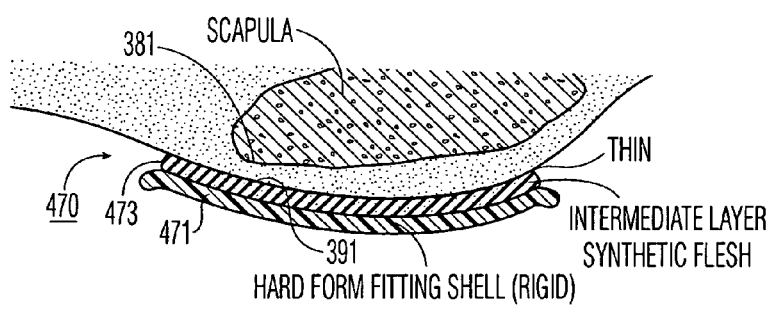

FIG. 18A is a cross sectional cut away view of a scapula with a hard shell prosthesis 470 placed between the scapula and a support surface. FIG. 18B is a blow up of the scapular section showing the conforming hard shell layer 471 and a soft liner section 473.

Hard Shell for Occiput

Figure 19:
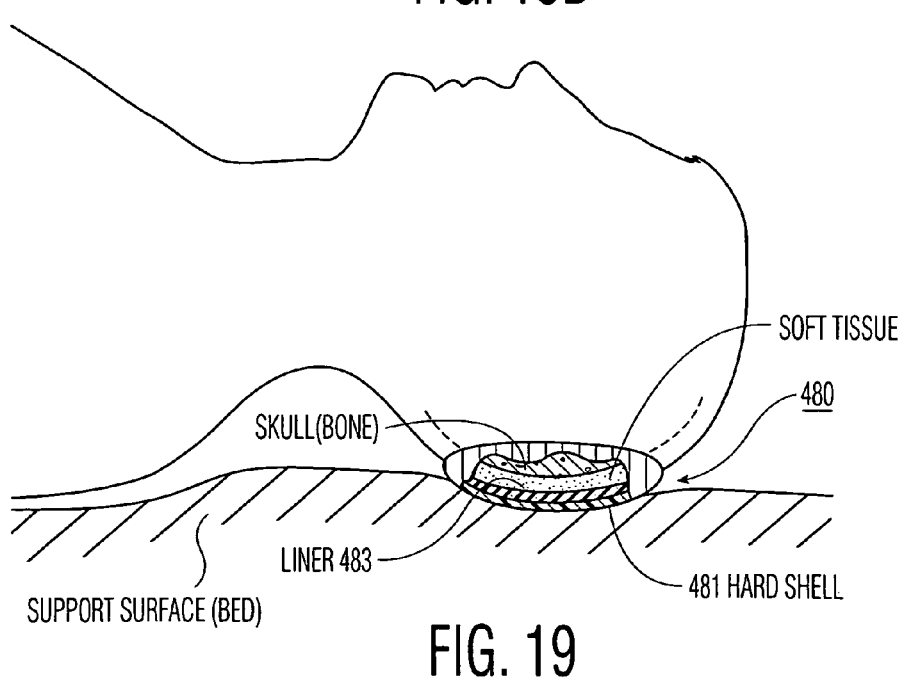
FIG. 19 is a cutaway cross sectional view of the occiput and a "hard" shell prosthesis for protecting that region.

FIG. 19 is a cross sectional cut away view of the occiput (similar to FIG. 11) with a hard shell prosthesis 480 placed along the back of the head. As for the other hard shell protective devices, prosthesis 480, may include a conforming hard shell 481 and a soft material liner 483.

Hard Shell for Elbow

Figure 20:
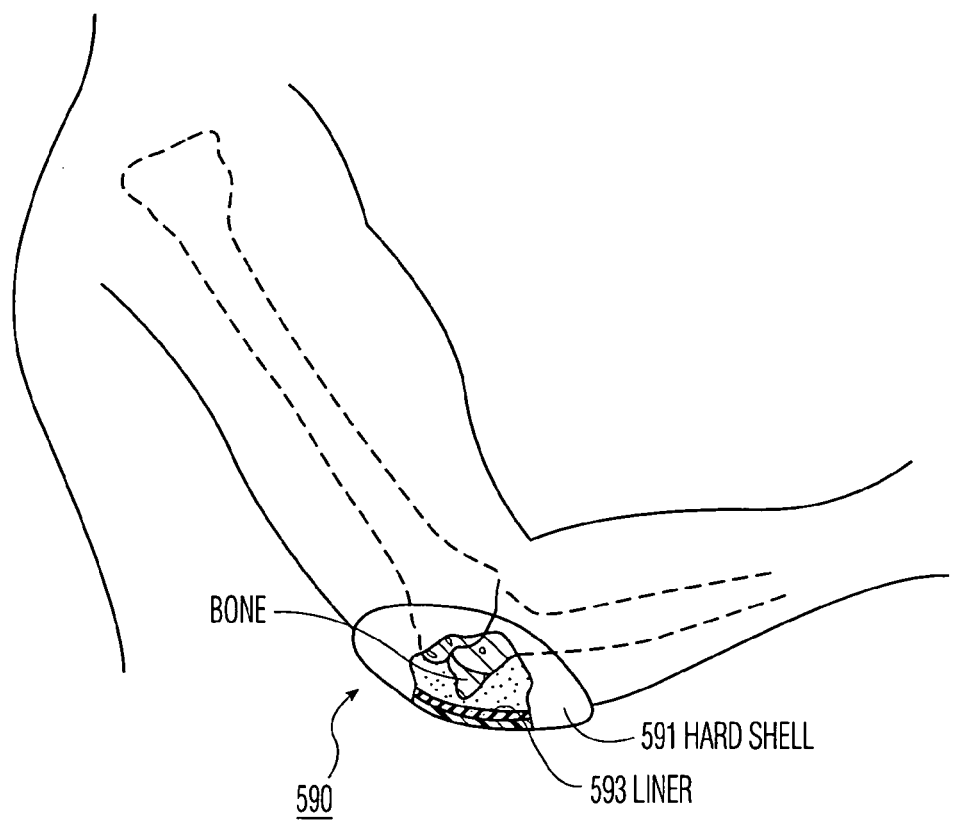
FIG. 20 is a cross sectional cutaway view of the elbow with a "hard" shell prosthesis for protecting that region.

FIG. 20 shows a cross section of a hard shell prosthesis 490 for use with the elbows. The prosthesis includes a hard shell 591 made to conform to the contour of the elbow of the user and a liner 593 made of soft material. As in the case of all the hard shell prostheses the liner may be a wound dressing material or any soft matter capable of easily conforming to the shape of the body part. The thickness of the liner may vary over a wide range while still providing the benefit of the high degree of conformal contouring of the underlying hard shell prosthesis.

Prostheses for Knees

Figure 24A:
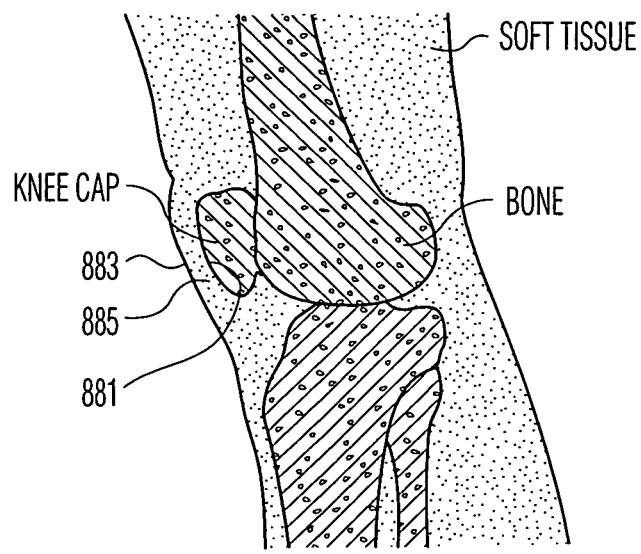
FIGS. 24A-24H show different views of the knee and views of a soft material prosthesis and a hard material prosthesis for application to the knee.
Figure 24B:
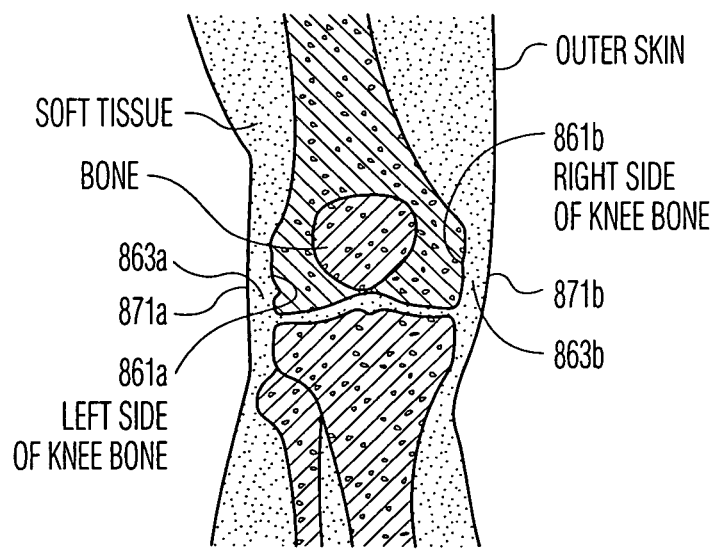
Figure 24C:
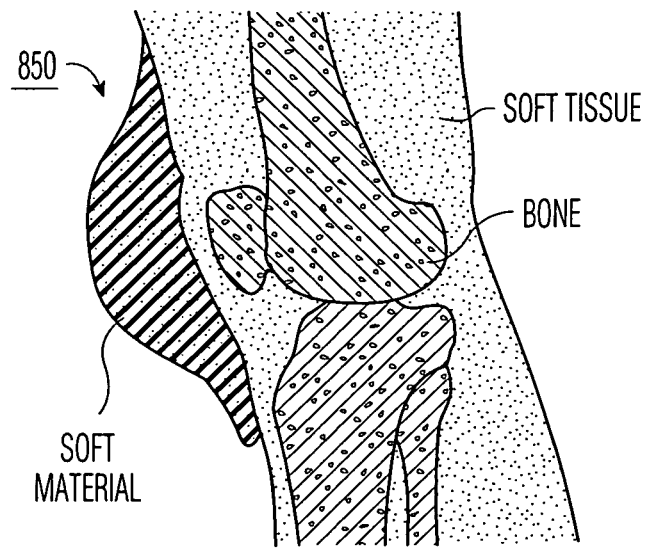
Figure 24D:
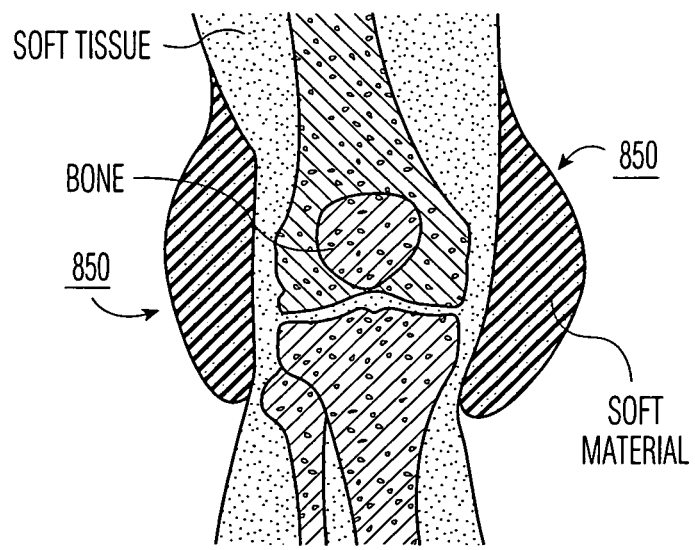
Figure 24E:
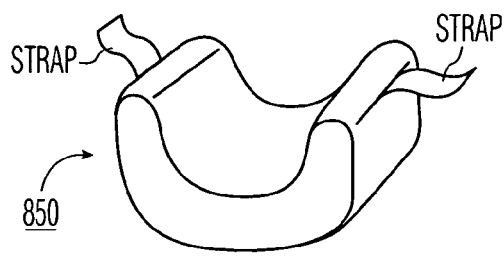
Figure 24E:
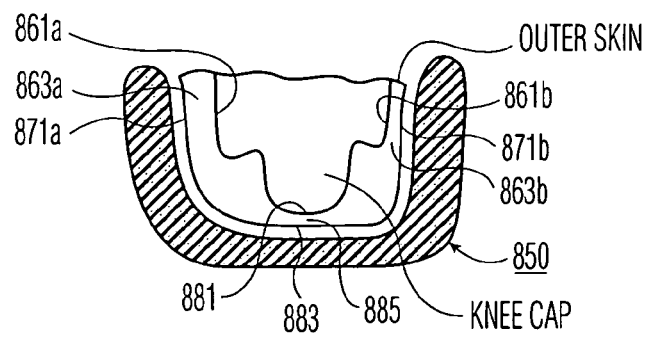

FIGS. 24A-24E are various views of the knees and of a soft prosthesis 850 for protecting the knee cap and both the inside and the outside portion of each knee. FIG. 24A is a side view of a knee showing a bony prominence 881 associated with the knee cap a corresponding outer skin region 883 and an intervening soft tissue layer 885. FIG. 24B is a front view of the knee of FIG. 24A, showing bony prominences 861a, 861b, corresponding outer skin regions 871a, 871b, and intervening soft tissue layers 863a, 863b. FIGS. 24C and 24D show a soft material prosthesis 850 suitable for protecting the kneecap and both sides of the knee. FIG. 24D is a perspective view of the prosthesis 850 including straps for attaching the prosthesis to the body. FIG. 24E is a cross section through the prosthesis and the knee section showing that the prosthesis protects the kneecap region as well as both sides of the knee.

Figure 24F:
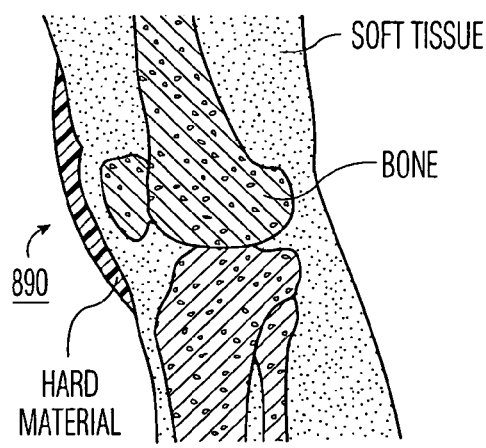
Figure 24G:
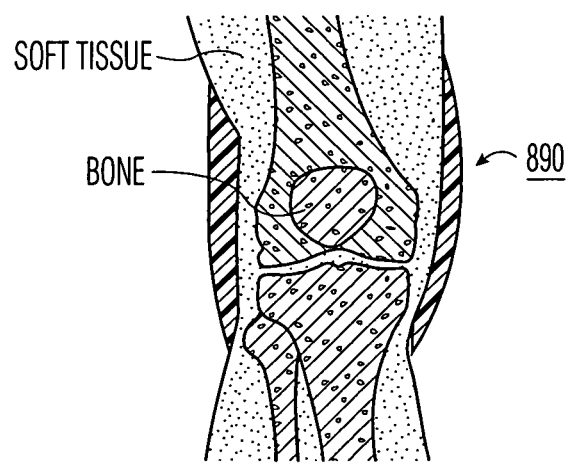
Figure 24H:

FIGS. 24F, 24G, and 24H show the application of a hard material prosthesis 890 to protect the kneecap region and both sides of the knee. The prosthesis, as shown in FIG. 24H, may include a thin, hard shell 891 and an inner liner 893. The hard shell prosthesis 890 would be made to conform to the shape and contour of the knee region even though, for reason of simplicity, this is not shown in the drawings. Also, though not shown, the hard shell prosthesis would be, or may be, hinged to enable movement of the user's legs. If needed, the hinging may be incorporated in the soft material prosthesis 850.

Prostheses for Buttocks

Figure 25C:
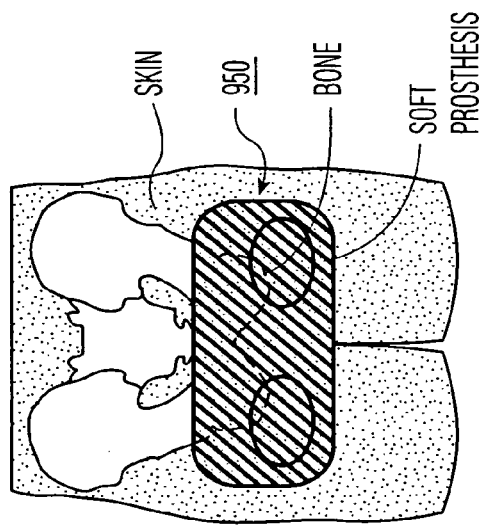
FIGS. 25A-25F show different views of the buttocks and views of a soft prosthesis and a hard material prosthesis for application to the buttocks.
Figure 25B:
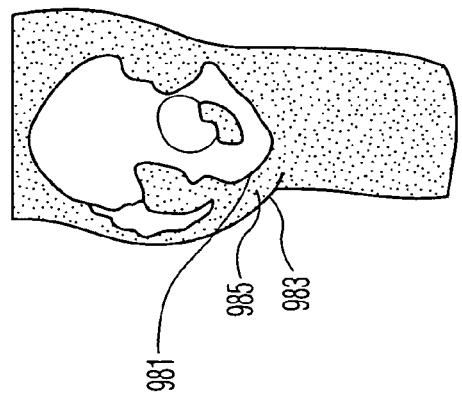
Figure 25A:
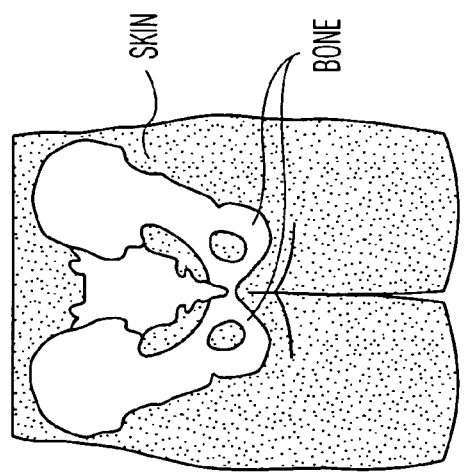
Figure 25F:
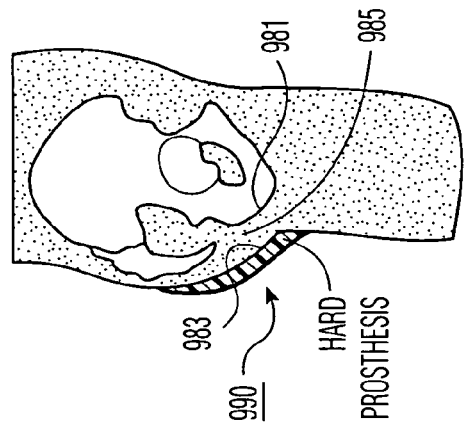
Figure 25E:
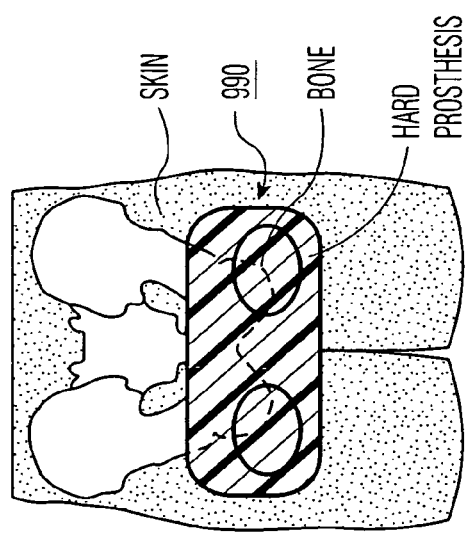
Figure 25D:
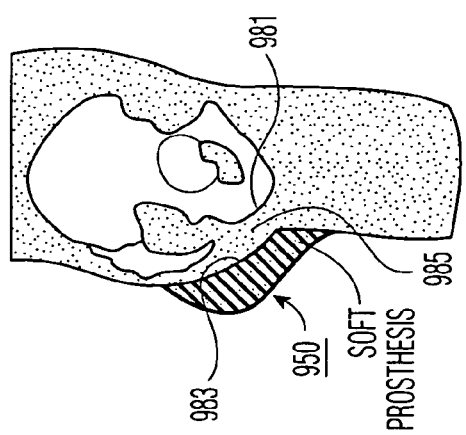

FIGS. 25A and 25B are, respectively, a rear view and a side view of the buttocks showing a bony prominence 981 an outer skin region 983 and an intervening soft tissue layer 985. FIGS. 25C and 25D show the application of a soft material prosthesis 950 to the buttocks region so as to reduce pressure between regions 981 and 983. FIGS. 25E and 25F show the application of a hard shell prosthesis 990 conforming to the region 983 to reduce the pressure between regions 981 and 983.

As in the case for the "soft" prostheses, it should be evident from the examples discussed above, that "hard" prostheses embodying Applicants' invention may be applied to reduce the pressure associated with any bony prominence. In fact, a wide range of materials may be used to practice the invention. The range is continuous and extends from materials whose stiffness moduli are greater than 1000 pounds per square inch (psi), which may be considered "very hard" materials, to materials whose stiffness moduli is less than 10 psi, which may be considered very soft materials. Applicants conducted a number of tests with a variety of materials demonstrating that the extent of the pressure reduction was a function of the contouring and thickness and that very hard materials as well as very soft materials could be used.

The individual protective devices thus far developed for the external application to the body parts may be clustered to include all of the locations of interest. By securing these units to assemblies as described below a system can be attained that gives each patient the level of protection from high pressures that he or she needs. These protective devices can be secured to stockings, panty hose, panty, shirt or body suit either within the garment or be affixed to the outside of the garment. Garment constructions can be used that have flaps at the critical locations which may be opened for insertion of a prosthesis. The utility of such a group of product modifications is very high since they will allow the caregivers of the patients to place the patient in bed, in a "geri" chair, and/or in a wheel chair, without any concern that a pressure ulcer will occur which can form only in bed (such as at the trochanter), or only in a chair (such as the ischium) when the patient is transferred from one support surface to another. One practical manifestation of this need is with nursing homes. It is common practice in good nursing homes to transfer the patient from the bed to a wheel chair or "geri" chair after breakfast, to transfer the patient from the chair to the bed for the afternoon nap, to transfer the patient back to the chair after the nap and then to transfer the patient back to bed for the night after supper. The system of prostheses described herein allows this routine to be performed without additional patient handling. This assures compliance on the part of the caregivers and less trauma or discomfort for the patients.

Assemblies suitable for enabling the application/attachment of more than one prosthesis at a time include, for example:
a) Full foot unit with prosthetic components for the heel and ankles;
b) Foot and leg unit with prosthetic components for the heel, ankles and knee;
c) Double foot and leg units with prosthetic components for the heel, ankles and knee on both legs;
d) Brief unit with prosthetic components for the trochanters, sacrum, coccyx, buttocks and ischia;
e) Panty hose unit with prosthetic components for both heels, both ankles, both knees, both trochanters, sacrum, coccyx and ischia;
f) Thorax unit with prosthetic components for the scapulae;
g) Thorax and arm unit with prosthetic components for the scapulae and elbows; and
h) Full body unit with prosthetic components for all the bony prominence(s).

Prostheses of Changeable Shape as a Function of Moisture

The prostheses concepts thus far considered are based on using materials which maintain stable compression properties during their usage. Applicants recognized that there is a relationship between the stiffness of the material used and the thickness of material required to achieve desired pressure reduction at the sites of interest. This relationship is that the stiffer the (conforming) material, the thinner the prosthesis required to achieve the desired results.

If a thin, stiff prosthesis of proper size, that conforms to the body part and site according to the teachings of the application is used, the desired effect of reduced pressure at the bony prominence soft tissue interface is obtained.

If a thicker, less stiff (or softer) prosthesis of proper size, that conforms to the site according to the teachings of the application, is used the desired effect is also obtained.

The site receiving the treatment cannot differentiate which prosthesis is being used to reduce the bone-soft tissue interface, When certain materials are hydrated, or otherwise allowed to expand by imbibing a fluid, they will expand from their initial thickness as the imbibing process occurs. Prior to hydration or imbibing, the material can have a dry, stiff structure that can be in sheet, powder and other forms consistent with firm dry materials. Such materials may also be formed into shapes that can be contoured around other shapes such as the body sites where pressure ulcers form.

It is to be understood that changes in areas of the prosthesis are included within this invention as they too will allow for proper level of pressure reduction by virtue of increasing the contact area between the prosthesis and the skin.

As the originally dry, or unswollen form absorbs or imbibes fluid, it becomes thicker (and, depending on the requirements, larger in area) and softer. The changes in thickness (and/or area) and stiffness are, to some degree, a function of the material properties. The rate of fluid absorption and the rate at which the absorbed fluid is transferred from the primary point contact with the source of fluid are properties which can be designed into the material. Depending on these properties, a device can be constructed that provides for absorption of fluid in a pattern that allows proper thickness (and/or area) and stiffness levels to be maintained to assure meeting the requirements for pressure reduction. It should be appreciated that the "fluid" may also be a gas, such as air. For example, a prosthesis may be constructed from a relatively rigid compressed foam elastomer, which is pre-shaped to the contour of a body site and then applied. As the patient (person) wears the prosthesis, the temperature of the patient may cause the foam to expand and become softer and thicker to provide pressure reduction.

Materials that can be considered for this application include, but are not limited to:
(a) Gel formers such as calcium alginate, gelatin and crosslinked polyethylene oxide.
(b) Gum formers such as carboxymethylcellulose, methylcellulose and guar gum.
(c) Compressed fibrous absorbents, such as cardboard.
(d) Compressed foam materials such as hydrophilic polyurethane foam.
(e) Combinations of the above.

FIGS. 21A-21D show the operation of such a device on a site of concern, the heel. It serves only as an example and this invention can be applied to all sites of interest.

Figure 21A:
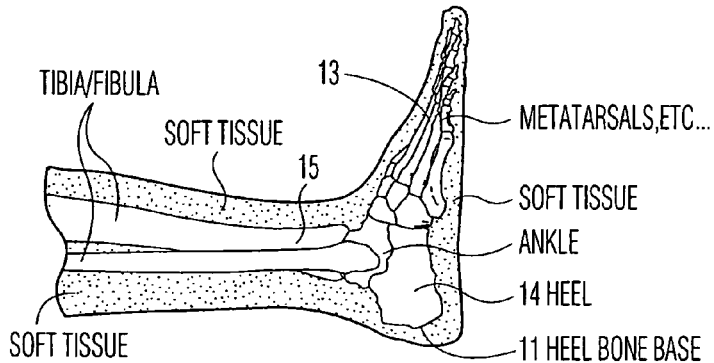
FIGS. 21A through 21D are various views of a prosthesis which undergoes change as a function of moisture absorption.

FIG. 21A is a cross section of the heel ankle region.

Figure 21B:
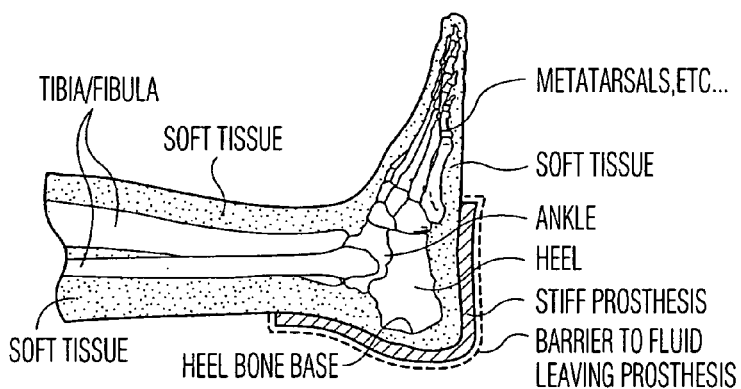

FIG. 21B illustrates the application of a "stiff" prosthesis below the heel region which runs continuously below the bottom of the foot. The stiff prosthesis is made to conform to the shape of the body part. Furthermore this prosthesis is made of the materials identified in (a)-(e), above, or in similar materials exhibiting like characteristics. Note that the thickness of the prosthesis both below the heel and below the foot is made relatively thin. The exterior portion of the prosthesis may include a barrier which inhibits any fluid from escaping. [Note: the fluid present and being absorbed may be due to medication (wound dressing) or due to moisture emitted by the body]. Therefore, any fluid at the body part will be absorbed by the prosthesis.

Figure 21C:
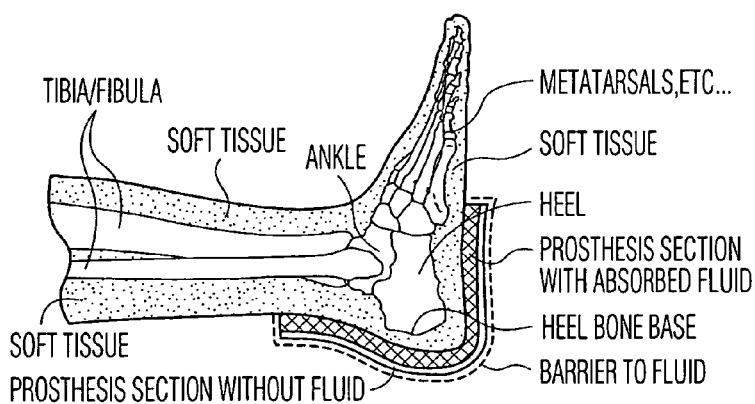

FIG. 21C shows the expansion of the thickness of the prosthesis as it absorbs fluid. As the prosthesis expands (i.e., becomes thicker) it also becomes softer and more compliant to the overlying body part whose weight is exerted onto the prosthesis, providing more area and volume to absorb the weight of the body part.

Figure 21D:
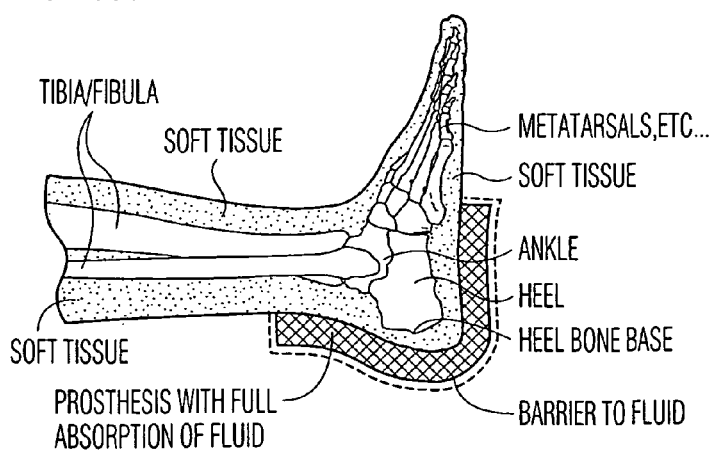
Figure 22A:
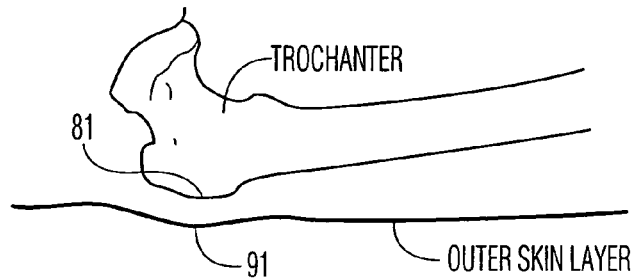
FIGS. 22A-22D illustrate implanting a prosthesis within a body part.
Figure 22B:
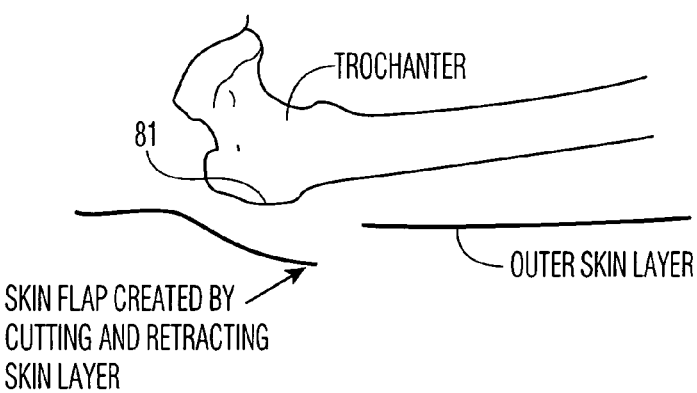
Figure 22C:
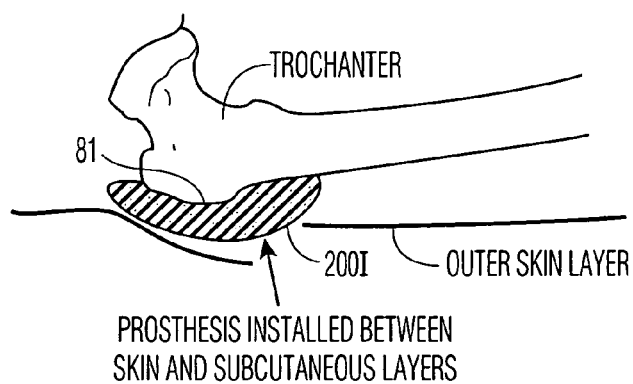
Figure 22D:
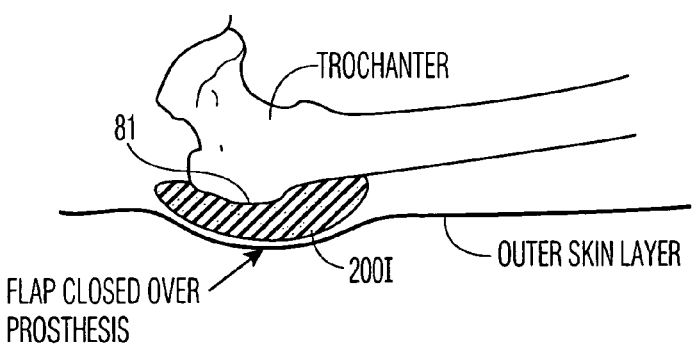

FIG. 21D shows that the prosthesis may have expanded significantly, absorbing the fluid being emitted by or around the body part, while providing pressure relief to the all parts of the body part being protected.

Discussion of Thickness of Soft Tissue and Testing

The thickness and softness of the soft tissue(s) between a bony prominence and the skin-mattress interface greatly affects the actual pressure experienced by the soft tissues at the bony prominence(s). As the weight and pressure radiate from the bony prominence towards the skin-mattress interface, the pressure at the bony prominence is reduced, and a greater reduction is experienced if the soft tissue is thicker and softer. Therefore, if a prosthesis embodying the invention consists at least, in part, of a "soft tissue" extension at the sites of concern, then the pressure at the bony prominence will be reduced.

By determining the actual thickness and softness of the soft tissue(s) of a patient sufficient additional "soft tissue" may be applied and/or attached at those sites to create a total soft tissue entity that will reduce the pressure at the bony prominence-soft tissue interface to an acceptable level. This occurs without necessarily impacting any other area of the body, especially those areas where the pressure at the bones is well within acceptable levels.

To validate this concept, tests were performed with a soft foam (referred to hereafter as mushy foam). In these tests, mushy foam samples were prepared having rectangular surfaces of 6 inches by 7 inches and with thicknesses varying from 0.5 inches to 2.5 inches. These samples were then applied to a mannequin to measure, with a sensor, changes in the internal heel pressure of the mannequin. The polymer thickness at the heel of the mannequin was 0.5 inches. [Note: In practice, these measurements of thickness would be made on a live patient, instead.] the following test were performed:
1. Determine baseline (no load) pressure reading on heel bone.
2. Determine maximum pressure reading on heel bone by placing heel directly on a firm foam mattress.
3. Determine baseline (no load) pressure reading on heel bone.
4. Place one mushy foam sample (for example 0.5 inches thick) on firm foam mattress and lower heel onto sample.
5. Determine pressure reading on heel bone by placing heel directly on the mushy foam sample.
6. Repeat steps (3) to (5) with mushy foam samples of different thicknesses until all have been tested.
7. Repeat entire process for a total of 4 replicates.
8. Cut cavities of 5 cm diameter.times.1.25 cm (0.5 inches) depth into center of mushy foam samples. The cavities function to make the sample conform more closely to the shape of the body part attached to the prosthesis. (For the 0.5 inch thick sample this created a hole in the sample).
9. Repeat steps (1) through (8) with these samples with the cutout.

FIG. 13B shows the internal pressure at the heel bone as a function of the thickness of a soft foam protective device. Each soft foam pad is a 6 inch by 7 inch rectangle cut to the thickness specified. It was placed on top of a firm foam mattress and the internal heel bone pressure was measured. A cutout was made in the sample having 5 centimeter diameter circle and being 1.25 cm deep (approximately 0.5 inches). The heel was placed in the cutout for these tests. For the 0.5 inch thick sample, making a cut out of 0.5 inches created a doughnut-like sample. However, prostheses embodying the invention do not rely on a doughnut effect to provide pressure reduction and weight redistribution.

Tests were conducted with the mannequin's foot resting on samples with cut outs and samples without cutouts. The test results indicate that better (lower pressure) results are obtained with cut outs. This is because there is greater surface area contact for this condition.

The findings from this study confirm that a 2 inch-thick mushy foam sample with a cutout can reduce the internal pressure at the bony prominence-soft tissue interface to an acceptable range to prevent pressure ulcer formation or allow an existing pressure ulcer to heal without patient turning. The sample and like devices can be incorporated as a prosthesis into, or onto, a dressing for treating such wounds where they already exist or become a prosthesis for the prevention of the ulcers in the first place. The mushy foam is very cheap and very easy to process into the shapes and thicknesses required to serve as an effective prosthesis. This allows protective devices embodying the invention to be a disposable item which may be sterilized if in use as part of a dressing, or to be non-sterile if in use to prevent ulcer formation.

Where the body or body part is placed on a support structure which is compliant (i.e., it deforms or conforms to accommodate the object placed thereon), then all compliant load bearing mediums may be considered as a composite structure for supporting the skeletal frame. This composite support structure comprises three components: (a) the patient's soft tissue against which the skeletal system (bone) comes into contact; (b) the protective device (prosthesis) which is interposed between the outer skin layer and the base support structure (i.e., bed mattress); and (c) the base (mattress or chair) which ultimately supports the overlying weight of the patient and prosthesis.

In accordance with the invention, the design of a soft prosthesis (i.e., one having foam like qualities) may include the compliance (softness) of the load bearing base (bed or chair) and the prosthesis itself as an integral part of the patient's soft tissue. If the load bearing base is non-compliant (hard), the prosthesis and the patient's soft tissue must distribute all the load within this volume so as to reduce the pressure seen at the bony prominence to less than a predetermined value (e.g., 32 mm Hg). If the load bearing base is compliant (soft), the compliance may be taken into account when calculating the load distribution characteristic of the overall composite structure. A more compliant base provides for some pressure distribution which results in a prosthesis design requiring less material volume and thickness. However, in most instances the prosthesis is designed assuming the base support to be non-compliant.

Figure 23B:
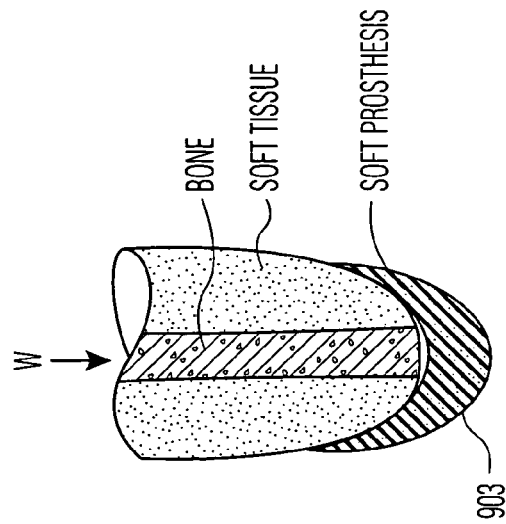
FIGS. 23A-23E illustrate an amputated body part and the application of prostheses embodying the invention for pressure reduction.
Figure 23A:
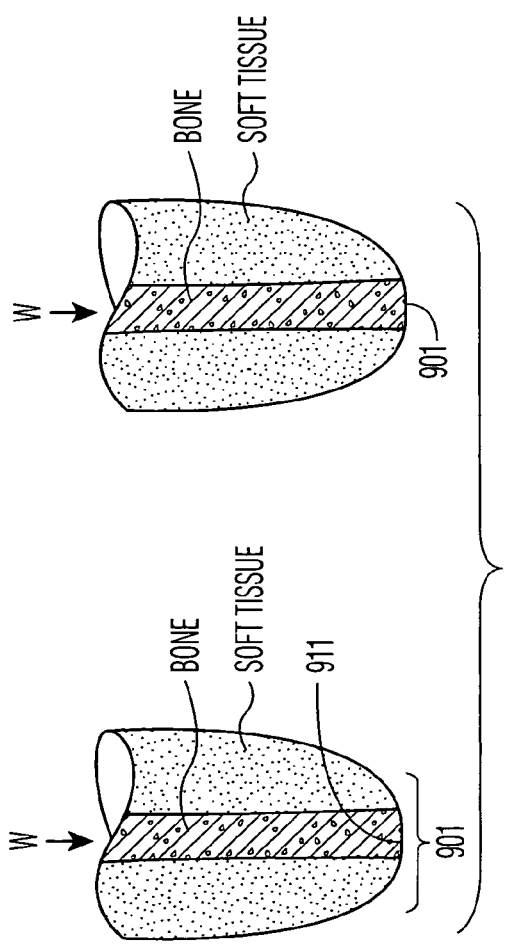
Figure 23E:
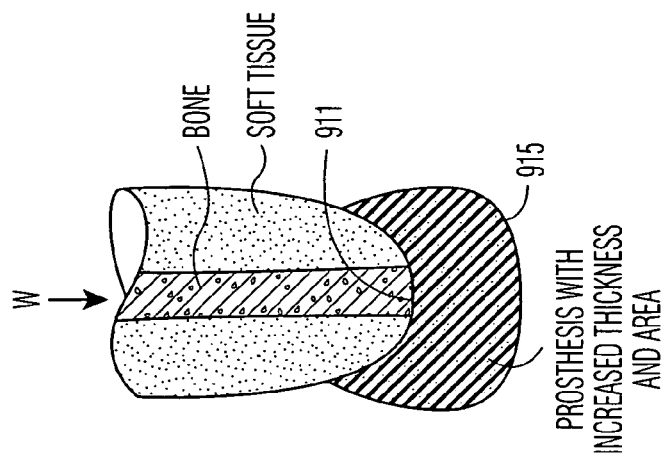
Figure 23D:
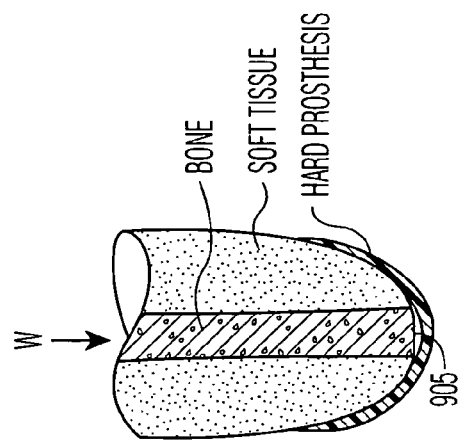
Figure 23C:
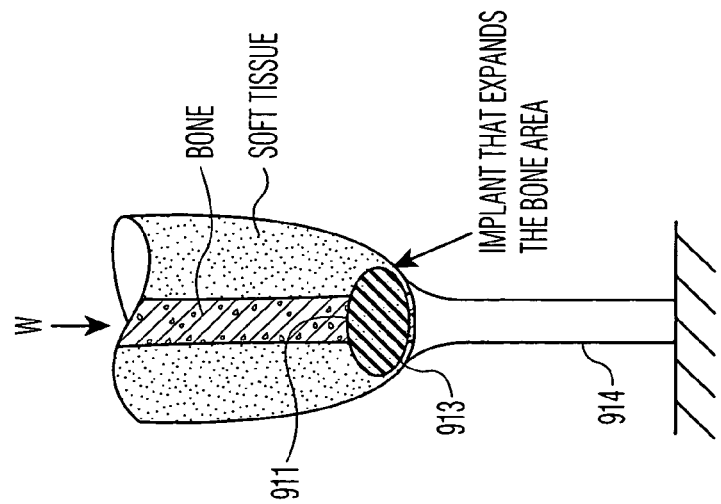

While the foregoing has been directed to pressure ulcers, it is understood that the invention can be applied to other pressure ulcer forming sites and/or conditions such as those associated with amputees, where a body "stump" is the site to be protected. FIG. 23A shows a portion of a leg amputated above the knee. The lower region may be outfitted with a soft prosthesis 903 as shown in FIG. 23B or with a hard prosthesis as shown in FIG. 23D. In keeping with the teachings of the invention, the bone section 911 may be effectively widened by the addition of an implant 913 to the bone section increasing the contact area of the bone section overlying the leg/foot support 914, as shown in FIG. 23C. Likewise, a prosthesis 915 with increased thickness and areas may be attached to the region 901 and bone 911 to provide greater area and volume to reduce pressure.

Internal Implanted Prosthesis

It is also understood that pressure relief may be obtained by implanting a prosthesis within a body part to effectively increase the thickness of the soft tissue layer around the bony prominence inside the body part. FIGS. 22A-22D show how a prosthesis 2001 would be installed around the trochanter, between the soft tissue layer underlying and surrounding the trochanter and the inner surface of the corresponding skin layer. Alternatively, the protective device 2001 would be installed around the trochanter between the trochanter and the underlying soft tissue layer. The implant 2001 could be a soft material or a hard material. A hard material implant could be used to effectively increase the surface area of any bony prominence so as to reduce any "sharp" bony points, as shown, for example in FIG. 23.

In addition to providing the required pressure relief, the various prostheses and prosthetic devices embodying the invention may include, or be entirely formed of, a "medicated" (or "non-medicated") dressing or material containing various substances to also provide "medical" protection and/or healing to the body part to which the prosthesis is attached. It should also be appreciated that the entire prosthesis, particularly where it is a "soft" prosthesis, may be constructed of material which may include a dressing or layer containing various substances to further protect the body part to which the prosthesis is attached. Thus, to provide additional medical protection to the outer skin and any proximate region of the body part the entire prosthesis or a dressing or layer on, or within, the prosthesis may include or consist of: (a) a dressing or a medicated dressing; (b) a hydrocolloid dressing by itself or containing medication including one or more of an anti-bacterial, anti-inflammatory, anti-fungal, and/or a pain killing substance; (c) a hydrogel by itself, or containing medication including one or more of an antibacterial, anti-inflammatory, anti-fungal, and/or a pain killing substance; (d) a thin film dressing by itself and/or containing medication including one or more of an antibacterial, anti-inflammatory, anti-fungal, and/or a pain killing substance; (e) a gauze dressing by itself and/or containing medication including one or more of an antibacterial, anti-inflammatory, anti-fungal, and/or a pain killing substance; (f) a non-woven dressing by itself and/or containing medication including one or more of an antibacterial, anti-inflammatory, anti-fungal, and/or a pain killing substance; (g) a foam dressing by itself and/or containing medication including one or more of an antibacterial, anti-inflammatory, anti-fungal, and/or a pain killing substance; (h) a fat-like substance, such as silicon or wax, which are generally deformable soft materials which exhibit little, if any, dimensional changes as a function of time; (i) material adapted to absorb any excess moisture and drainage; (j) material which exhibits moisture vapor permeability for removal of excess moisture to reduce maceration to the skin; (k) material which exhibits permeability to air for enabling air circulation for removing excess heat and moisture; and (l) any material containing medication including one or more of an antibacterial, anti-inflammatory, anti-fungal, and/or a pain killing substance.

It should be appreciated that the prostheses themselves, or layers of materials added to the prostheses, may incorporate substances providing for tissue seeding, tissue incorporation and tissue growth.

In the discussion above, the weight of a body part or the body illustrates one type of load which can lead to pressure ulcers. Other types of loads that can lead to pressure ulcers include, for example, tight fitting shoes and prosthetic devices, such as an artificial arm or leg, which is too tightly (or improperly) connected to a limb of an amputee. Shear forces as well as compression forces and a combination of these forces can lead to pressure ulcers.

Figure 26:
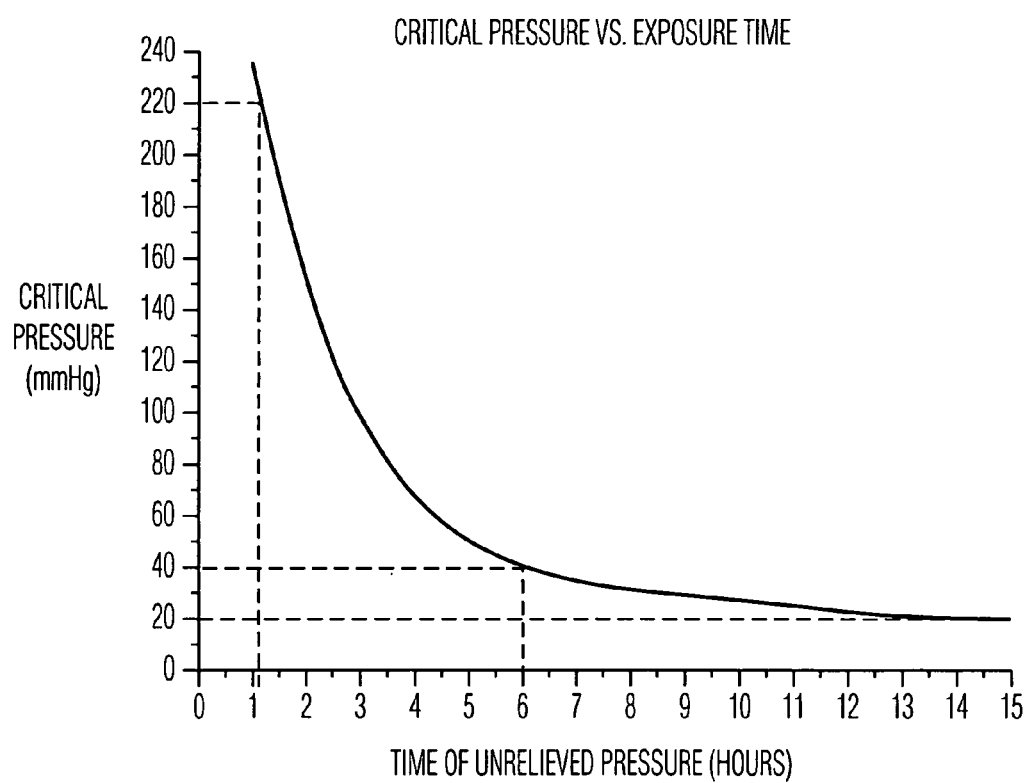
FIG. 26 is a graph of the critical pressure at which a pressure ulcer may form as a function of the length of time the pressure is applied.

It should be noted that pressure ulcers develop as a function of the pressure applied as a function of time. To better explain this point reference is made to FIG. 26 which shows a graph of critical pressure as a function of time the body part is exposed to the pressure. Thus, a pressure of 220 mm of Hg applied for 1-2 hours at a certain site will cause a pressure ulcer to develop. On the other hand it would take a pressure of 40 mm of Hg to be applied for 6 hours to cause a pressure ulcer to develop at that site. Furthermore, where the pressure is less than 20 mm of Hg, it would take at least 15 hours for this pressure to cause a pressure ulcer.

What is claimed is:

1. A protective device for protecting a human body part, such as the heel and the area around its bony prominence, where the bony prominence is the heel bone, and where a soft tissue layer extends between the bony prominence and an outer skin layer and wherein the bony prominence tends to concentrate the weight (W) of its associated body part over a small area (A1) and produce a compressive force due to a pressure (P1), which is equal to W/A1 at the interface between the bony prominence and its corresponding soft tissue layer when the body part is in direct contact with a support surface, and wherein P1 when applied for a time t1 tends to cause a pressure ulcer to develop in the body part associated with the bony prominence, the protective device comprising:
   a pad to be positioned between the support surface and the heel, said pad including a layer of material having a thickness profile and said pad having:
      (a) a top, inner, surface extending under and in direct and continuous contact with the heel and its associated bony prominence; and said top inner surface shaped to be conformable to the body part and its associated bony prominence for hugging, supporting and being in continuous contact with the heel and its associated bony prominence, whereby, when the heel and its associated bony prominence rests on the pad positioned along the support surface, the weight of the heel and its associated bony prominence are simultaneously and respectively distributed over a large portion of the area and volume of the pad and the weight (W) of the heel is no longer concentrated at the bony prominence and the effective weight present at the bony prominence is reduced, being less than W and the pressure is reduced, being less than P1, thereby reducing the compressive force developed at the interface between the bony prominence and its corresponding soft tissue layer; and
      (b) a, bottom, outer surface suitable for making contact with the support structure; and
   wherein the inner surface of the pad conforms to, and maintains direct contact and conformity with, the shape of the heel and the area about its bony prominence, and the outer surface of the pad making contact with the support structure is constructed to reduce shear forces applied to the heel due to movement of the heel along and about the support surface; and
   wherein the top inner surface of the pad is sculpted to form a groove to receive the heel and the back of the heel region and the lower leg; and
   wherein said groove includes a curvilinear cut out attached to a tubular region, the curvilinear cut out for receiving the heel and the tubular region for receiving the back of the heel and the lower leg.

2. A protective device as claimed in claim 1, wherein said bottom outer surface includes a layer of relatively smooth material for reducing friction due to movement of the heel and its associated bony prominence along the surface of the support surface.

3. A protective device as claimed in claim 1 wherein the inner surface of the pad material extending under, and in contact with, the heel and its associated bony prominence is one of an elastic material, a compliant mushy foam, a generally compliant material and a mesh material; and wherein the outer surface of the pad is of elastomeric or viscoelastic material for reducing friction and the application of shear, as well as pressure, forces to the body part to be protected as a result of movement of the body part along the support surface.

4. A protective device as claimed in claim 1, wherein the pad is formed to extend under the heel and its associated bony prominence so the weight (W) of the heel is distributed over a much larger area including the heel and its bony prominence whereby the pressure developed at any point along the bony prominence and the heel is less than P1.

5. A protective device as claimed in claim 1, wherein the pad is shaped to provide support for a portion of the heel adjacent the bony prominence to cause the effective weight at the bony prominence to be redistributed such that the weight at the bony prominence is significantly less than W, whereby the resulting pressure between the bony prominence and its underlying soft tissue layer is equal to P2, where P2 is less than P1, and P2 is less than a critical value of pressure which would tend to cause ulcers in the body part within the time t1.

6. A protective device as claimed in claim 1 wherein the pad material is of the type which enables its inner surface to conform to, surround, and hug the body part containing the bony prominence and wherein the pad includes along its top inner surface one of: (a) a dressing or a medicated dressing; (b) a hydrocolloid dressing by itself or containing medication including one or more of an antibacterial, anti-inflammatory, anti-fungal, and/or a pain killing substance; (c) a hydrogel by itself, or containing medication including one or more of an antibacterial, anti-inflammatory, anti-fungal, and/or a pain killing substance; (d) a thin film dressing by itself and/or containing medication including one or more of an antibacterial, anti-inflammatory, anti-fungal, and/or a pain killing substance; (e) a gauze dressing by itself and/or containing medication including one or more of an antibacterial, anti-inflammatory, anti-fungal, and/or a pain killing substance; (f) a non-woven dressing by itself and/or containing medication including one or more of an antibacterial, anti-inflammatory, anti-fungal, and/or a pain killing substance; (g) a foam dressing by itself and/or containing medication including one or more of an antibacterial, anti-inflammatory, anti-fungal, and/or a pain killing substance; (h) a fat-like substance, such as silicon or wax, which are generally deformable soft materials which exhibit little, if any, dimensional changes as a function of time; (i) material adapted to absorb any excess moisture and drainage; (j) material which exhibits moisture vapor permeability for removal of excess moisture to reduce maceration to the skin; (k) material which exhibits permeability to air for enabling air circulation for removing excess heat and moisture; and (I) any material containing medication including one or more of an antibacterial, anti-inflammatory, anti-fungal, and/or a pain killing substance.

7. A protective device as claimed in claim 1, wherein the pad extends continuously beneath the ankle region, the foot and the heel and the shape of the pad is one of the following: rectangular, cylindrical, semi-cylindrical, toroidal, ellipsoid, oblong, triangular and a combination thereof; and wherein the pad's outer surface is intended to lie along the support surface.

8. A protective device for protecting a human body part, such as (a) the heel, (b) the trochanter, (c) the sacrum, (d) the buttocks (e) the coccyx and (f) the ankle, where each one of said human body part includes a bony prominence and a soft tissue layer between the bony prominence and an outer skin layer and wherein each bony prominence tends to concentrate the weight (W) of its associated body part over a small area (A1) and produce a compressive force due to a pressure (P1), which is equal to W/A1 at the interface between the bony prominence and its corresponding soft tissue layer when the body part is in direct contact with a support surface, and wherein P1 when applied for a time t1 tends to cause a pressure ulcer to develop in the body part associated with the bony prominence, the protective device comprising:

a pad to be positioned between the support surface and the body part to be protected, said pad including a layer of material having a thickness profile and said pad having:

(a) a top, inner, surface extending under and in direct and continuous contact with the body part to be protected and its associated bony prominence; and said top inner surface shaped to be conformable to the body part and its associated bony prominence for hugging, supporting and being in continuous contact with the body part and its associated bony prominence, whereby when the body part and its associated bony prominence rests on the pad positioned along the support surface the weight of the body part and its associated bony prominence are simultaneously and respectively distributed over a large portion of the area and volume of the pad and the weight (W) of the body part is no longer concentrated at the bony prominence and the effective weight present at the bony prominence is reduced, being less than W and the pressure is reduced, being less than P1, thereby reducing the compressive force developed at the interface between the bony prominence and its corresponding soft tissue layer; and (b) a, bottom, outer surface suitable for making contact with the support structure; and (c) wherein the inner surface of the pad is shaped to conform to the shape of the body part and its associated bony prominence in order to increase the area over which the weight of the body part and its associated bony prominence is distributed; and wherein the thickness of the pad is at least 0.01 of an inch and extends continuously between the bony prominence and its associated body part to the support surface to provide a weight distribution cone along the thickness of the pad for increasing the effective area over which the concentrated weight present at the bony prominence is distributed, whereby a greater portion of the weight is radially distributed through the pad to the support surface, and thereby reducing the pressure at the interface between the bony prominence and its corresponding soft tissue layer, across the corresponding soft tissue layer and at the interface between the corresponding soft tissue layer and the corresponding outer skin and between the corresponding outer skin and the inner surface of the protective device whose outer surface is intended to be in contact with the support surface.

9. A protective device as claimed in claim 8, wherein the body part to be protected is the sacrum and wherein the inner surface of the pad extends above and below the sacrum and includes a notch in the top inner surface to conform to the shape of the sacrum, while maintaining contact with the sacrum, and wherein the outer surface of the pad is generally conformable to the support surface.

10. A protective device as claimed in claim 8 wherein selected properties of the pad applied to the body part, including its size, softness, thickness, construction design and materials, change as a function of the length of time the body part is to be on the support surface, or in response to environmental conditions such as temperature and moisture, so as to dynamically reduce the pressure and shear applied to the body part and to dynamically provide additional protection to the body part.

11. A protective device as claimed in claim 8 wherein the body part to be protected is the heel and the area about its bony prominence, where the bony prominence is the heel bone, and wherein the inner surface of the pad conforms to, and maintains direct contact and conformity with, the shape of the heel and the area about its bony prominence, and the outer surface of the pad making contact with the support structure is constructed to reduce shear forces applied to the heel due to movement of the heel along and about the support surface.

12. A protective device as claimed in claim 8 wherein each pad is shaped and contoured around its corresponding body part and attached to its body part to be in intimate contact with it so as to enable the body part to move in any direction and assume any normal orientation and to protect the body part regardless of the orientation of the body part on, or off, the support structure.

13. A protective device as claimed in claim 8, wherein the top surface of the protective device is sculpted to hug, and conform to, the shape of the body part to be protected whereby the body part containing the bony prominence is positioned within the sculpted region for maintaining conformity and intimate contact with the body part and the region of its bony prominence for ensuring that the increase in surface area over which the weight of the body part and the bony prominence is distributed is maintained under pressure.

14. A protective device as claimed in claim 8 wherein the thickness between the top and bottom surfaces is at least one quarter (¼) of an inch and the material between the top and bottom surfaces being one of an elastic material, a mushy foam, a mesh material, and materials including, but not limited to, dressings, fibrous absorbents, fat-like substance such as silicone or wax, fleeces, foam, gauze, gels, hard shell conforming materials, hydrocolloids, moisture absorbing materials, moisture removing materials, permeable materials, materials which may change in thickness and stiffness, viscoelastic materials and a combination of the above.

15. A protective device as claimed in claim 8 wherein said pad includes a layer of material having wound dressing properties and
wherein said bottom outer surface of said pad includes a layer of a material having a texture for controlling the development and application of shear, friction and pressure forces to the body part and its associated bony prominence due to movement of the body part along the surface of the support surface.

16. A protective device as claimed in claim 8 wherein the body part to be protected is the sacrum or the heel or the ankle and wherein the pad is attached to the body area about the sacrum or the heel or the ankle and applied so as to extend between the sacrum or the heel or the ankle and the support surface and wherein the pad surrounds the sacrum or the heel or the ankle and extends above and below the sacrum or the heel or the ankle and the pad has an inner surface and with a groove corresponding to the bony prominence of the sacrum or the heel or the ankle which contacts and conforms to, and hugs, the sacrum or the heel or the ankle so as to simultaneously distribute the weight at the bony prominence of the sacrum or the heel or the ankle and its associated body part via the pad hugging the body part containing the bony prominence, and the pad has an outer surface suitable for making contact with the support surface and reducing shear forces when the human body moves along the support surface.

17. A protective device as claimed in claim 8, wherein the pad includes one of the following:
(a) a dressing or a medicated dressing;
(b) a hydrocolloid dressing by itself or containing medication including one or more of an antibacterial, anti-inflammatory, anti-fungal, and/or a pain killing substance;
(c) a hydrogel by itself, or containing medication including one or more of an antibacterial, anti-inflammatory, anti-fungal, and/or a pain killing substance;
(d) a thin film dressing by itself and/or containing medication including one or more of an antibacterial, anti-inflammatory, anti-fungal, and/or a pain killing substance;
(e) a gauze dressing by itself and/or containing medication including one or more of an antibacterial, anti-inflammatory, anti-fungal, and/or a pain killing substance;
(f) a non-woven dressing by itself and/or containing medication including one or more of an antibacterial, anti-inflammatory, anti-fungal, and/or a pain killing substance;
(g) a foam dressing by itself and/or containing medication including one or more of an antibacterial, anti-inflammatory, anti-fungal, and/or a pain killing substance;
(h) a fat-like substance, such as silicon or wax, which are generally deformable soft materials which exhibit little, if any, dimensional changes as a function of time;
(i) material adapted to absorb any excess moisture and drainage;
(j) material which exhibits moisture vapor permeability for removal of excess moisture to reduce maceration to the skin;
(k) material which exhibits permeability to air for enabling air circulation for removing excess heat and moisture; and
(l) any material containing medication including one or more of an antibacterial, anti-inflammatory, anti-fungal, and/or a pain killing substance.

18. A protective device for protecting a human body part, such as the heel and the area about its bony prominence which is the heel bone, and where a soft tissue layer extends between the bony prominence and an outer skin layer and wherein the bony prominence tends to concentrate the weight (W) of its associated body part over a small area (A1) and produce a compressive force due to a pressure (P1), which is equal to W/A1 at the interface between the bony prominence and its corresponding soft tissue layer when the body part is in direct contact with a support surface, and wherein P1 when applied for a time t1 tends to cause a pressure ulcer to develop in the body part associated with the bony prominence, the protective device comprising:
a pad to be positioned between the support surface and the body part to be protected, said pad including a layer of material having a thickness profile and said pad having:
(a) a top, inner, surface extending under and in direct and continuous contact with the body part to be protected and its associated bony prominence; and said top inner surface shaped to be conformable to the body part and its associated bony prominence for hugging, supporting and being in continuous contact with the body part and its associated bony prominence, whereby, when the body part and its associated bony prominence rests on the pad positioned along the support surface, the weight of the body part and its associated bony prominence are simultaneously and respectively distributed over a large portion of the area and volume of the pad and the weight (W) of the body part is no longer concentrated at the bony prominence and the effective weight present at the bony prominence is reduced, being less than W and the pressure is reduced, being less than P1, thereby reducing the compressive force developed at the interface between the bony prominence and its corresponding soft tissue layer; and (b) a, bottom, outer surface suitable for making contact with the support structure;

and wherein the top inner surface of the pad includes a wound dressing layer which conforms to, and maintains direct contact and conformity with, the shape of the heel and the area about its bony prominence.

19. A protective device as claimed in claim 18 wherein the wound dressing layer aids in securing the heel to the pad without the need for any other securing means.

20. A protective device as claimed in claim 18 wherein the wound dressing layer is deployed to cause a reduction in the pressure at the heel region tending to enable more effective wound healing or wound prevention.

* * * * *